United States Patent
Sedlacek et al.

(12)

(10) Patent No.: US 6,235,526 B1
(45) Date of Patent: May 22, 2001

(54) NUCLEIC ACID CONSTRUCTS CONTAINING GENES ENCODING TRANSPORT SIGNALS

(75) Inventors: Hans-Harald Sedlacek; Rolf Mueller; Reinhard Luehrmann, all of Marburg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 08/850,744

(22) Filed: May 2, 1997

(30) Foreign Application Priority Data

May 3, 1996 (DE) ................................ 196 17 851

(51) Int. Cl.[7] .............. C12N 5/10; C12N 15/63

(52) U.S. Cl. ............ 435/325; 435/320.1; 435/357; 435/366; 536/23.1; 536/24.1

(58) Field of Search ................ 435/320.1, 325, 435/357, 366; 536/23.1, 23.72, 24.1

(56) References Cited

U.S. PATENT DOCUMENTS

| | | | |
|---|---|---|---|
| 5,464,758 | 11/1995 | Gossen et al. | 435/69.1 |
| 5,604,114 * | 2/1997 | Haseltine et al. | 435/69.1 |
| 5,830,880 | 11/1998 | Sedlacek et al. | 514/44 |
| 5,854,019 | 12/1998 | Sedlacek et al. | 435/69.1 |
| 5,885,833 | 3/1999 | Sedlacek et al. | 435/372 |
| 5,916,803 | 6/1999 | Sedlacek et al. | 435/320.1 |

FOREIGN PATENT DOCUMENTS

| | | |
|---|---|---|
| 0 464 633 A1 | 6/1991 | (EP) . |
| 0 511 917 A1 | 4/1992 | (EP) . |
| 92/21750 | 12/1992 | (WO) . |
| 94/20621 | 9/1994 | (WO) . |
| WO 95/21927 | 8/1995 | (WO) . |
| WO 96/05994 | 2/1996 | (WO) . |
| 96/09392 | 3/1996 | (WO) . |
| WO 96/06938 | 3/1996 | (WO) . |
| WO 96/06940 | 3/1996 | (WO) . |
| WO 96/06941 | 3/1996 | (WO) . |
| WO 96/06943 | 3/1996 | (WO) . |

OTHER PUBLICATIONS

Bevec et al. (1994) Constitutive expression of chimeric Neo–rev response element transcripts suppresses HIV–1 replication in human CD4+ T lymphocytes. Human Gene Ther. 5:193–201, Feb. 1994.*

Zimmermann et al. (1992) Expression of chimeric Neo–rev response element sequences interferes with rev–dependent HIV–1 gag expression. Human Gene Ther. 3:155–161, Apr. 1992.*

Gazit et al. (1996) Two species of rev proteins, with distinct N termini, are expressed by caprine arthritis encephalitis virus. J. Virol. 70:2674–2677, Apr. 1996.*

W.M. Michael et al., "Signal Sequences that Target Nuclear Import and Nuclear Export of Pre–mRNA–binding Proteins", Cold Spring Harbor Symposia on Quantitative biology, Bd. 60 Nr. 0, 1995, p. 663–68.

W. Michael et al., "A Nuclear Export Signal in hnRNP A1: A Signal–Mediated, Temperature–Dependent Nuclear Protein Export Pathway", Cell, vol. 83, No. 1995, p. 415–422.

Junginger, H–E, et al., "Liposomen und Niosomen—Herstellung und Prüfung", Jahrgang, pp. 1631–1641, 1991 (Abstract).

Nicholas B La Thangue, "DP and E2F proteins: components of a heterodimeric transcription factor implicated in cell cycle control", Current Biology, pp. 443–450, 1994.

Lafage, M., et al., "The Human Interleukin–1α Gene Is Located on the Long Arm of Chromosome 2 at Band q13", Blood, vol. 73, No. 1, pp. 104–107, 1989.

Lage, A., et al., "*H. pylori* Vacuolating Toxin and Gastric Cancer", Acta Gastro–Enterologica Belgica, p. 61, 1993.

Lemon, S.M., et al., "Genetic, antigenic and biological differences between strains of hepatitis A virus", Vaccine, vol. 10, Suppl. 1, pp. S40–S44, 1992.

Leuther, K.K., et al., "Nondissociation of GAL4 and GAL80 in Vivo After Galactose Induction", Science, vol. 256, pp. 1333–1335, 1992.

Levine, et al., "Live oral vaccines against cholera: an update", Vaccine, vol. 11, Issue 2, pp. 207–212, 1993.

Lichtenstein, et al., "Definition and functional analysis of the signal/anchor domain of the human respiratory syncytial virus glycoprotein G", J. of General Virology, vol. 77, pp. 109–118, 1996.

Maddon, et al., "The Isolation and Nucleotide Sequence of a cDNA Encoding the T Cell Surface Protein T4: A New Member of the Immunoglobulin Gene Family", Cell, vol. 42, pp. 93–104, 1985.

Malim, et al., "The HIV–1 rev trans–activator acts through a structural target sequence to activate nuclear export of unspliced viral mRNA", Nature, vol. 338, pp. 254–257 1989.

Malim, H.M., et al., "HIV–1 Structural Gene Expression Requires the Binding of Multiple Rev Monomers to the Viral RRE: Implications for HIV–1 Latency", Cell, vol. 65, pp. 241–248, 1991.

Malim, M.H., et al., "Mutational Definition of the Human Immunodeficiency Virus Type 1 Rev Activation Domain", J. of Virology, pp. 4248–4254, 1991.

(List continued on next page.)

Primary Examiner—Robert A. Schwartzman
(74) Attorney, Agent, or Firm—Heller Ehrman White & McAuliffe LLP

(57) ABSTRACT

Nucleic acid constructs are disclosed which possess a nuclear retention signal which is linked, downstream in the reading direction, to a transgene. The nuclear retention signal can regulate the presence of the transcription product in the cell nucleus or else the intracellular transport of the transcription product.

49 Claims, 8 Drawing Sheets

OTHER PUBLICATIONS

Mandell, R. B., et al., "Identification of Two HSP70–related Xenopus Oocyte Proteins That Are Capable of Recycling Across the Nuclear Envelope", J. of Cell Biol., vol. 111, pp. 1775–1783, 1990.

Mancuso, V.A., et al., "Posttranscriptional Effector Domains in the Rev Proteins of Feline Immunodeficiency Virus and Equine Infectious Anemia Virus", J. of Virology, pp. 1998–2001, 1994.

Marasco, W.A., et al., "Design, intracellular expression, and activity of a human anti–human immunodeficiency virus type 1 gp120 single–chain antibody", Proc. Natl. Acad. Sci, USA, vol. 90, pp. 7889–7893, 1993.

March, C.J., et al., "Cloning, sequence and expression of two distinct human interleukin–1 complementary DNAs", Nature, vol. 315, pp. 641–647, 1985.

Maruyama, K. et al., "Lipid composition is important for highly efficient target binding and retention of immunoliposomes", Proc. Natl. Acad. Sci., USA, vol. 87, pp. 5744–5748, 1990.

Matsui, H., et al., "Molecular Cloning and Expression of the Human Interleukin 2 Gene" Lymphokines, vol. 12, pp. 1–12, 1985.

Maurice, J., "Malaria Vaccine Raises a Dilemma", Science, vol. 267, pp. 320–323, 1995.

McBurney, M.W., et al., "The mouse Pgk–1 gene promoter contains an upstream activator sequence", Nucleic Acids Research, vol. 19, No. 20, pp. 5755–5761, 1991.

Means, A.L., et al., The HIP1 Binding Site Is Required for Growth Regulation of the Dihydrofolate Reductase Gene Promoter, Mol. and Cell. Biol., vol. 12, No. 3, pp. 1054–1063, 1992.

Melnick, J.L., "Properties and classification of hepatitis A virus", Vaccine, vol. 10, Suppl. 1, S24–S26, 1992.

Mobley, H.L.T., et al., "*Helicobacter pylori* Urease: Properties and Role in Pathogenesis", Scand. J. Gastroenterol., Suppl. 187, pp. 39–46, 1991.

Morrissey, J.H., et al., "Molecular Cloning of the cDNA for Tissue Factor, the Cellular Receptor for the Initiation of the Coagulation Protease Cascade", Cell, vol. 50, pp. 129–135, 1987.

Muesing, M.A., et al., "Nucleic acid structure and expression of the human AIDS/lymphadenopathy retrovirus," Nature, vol. 313, pp. 450–458, 1985.

Müller, R., "Transcriptional regulation during the mammalian cell cycle", Trends in Genetics, vol. 11, No. 173, pp. 1–19, 1995.

Nicola, N.A., et al., "Similar Molecular Properties of Granulocyte–Macrophage Colony–stimulating Factors Produced by Different Mouse Organis in Vitro and in Vivo*", J. of Biological Chemistry, vol. 254, No. 12, pp. 5290–5299, 1979.

Nussenzweig, R.S., et al., "Malaria Vaccines: Multiple Targets", Science vol. 265, pp. 1381–1383, 1994.

O'Keefe, M.C., et al., "A Novel Cleavage Product of Human Complement Component C3 with Structural and Functional Properties of Cobra Venom Factor*", J. of Biological Chemistry, vol. 263, No. 25, pp. 12690–12697, 1988.

Pauli, B. U., et al., "Organ–preference of metastasis", Cancer and Metastasis Reviews, vol. 9, pp. 175–189, 1990.

Perlmutter, R.M., et al., "Structure and Expression of lck Transcripts in Human Lymphoid Cells", J. of Cellular Biochemistry, vol. 38, pp. 117–126, 1988.

Piñol–Roma, S., et al., "Shuttling of pre–mRNA binding proteins between nucleus and cytoplasm", Nature, vol. 355, pp. 730–732, 1992.

Plotkin, S.A., "Vaccines for Varicella–Zoster Virus and Cytomegalovirus: Recent Progress," Science, vol. 265, pp. 1383–1385, 1994.

Pusztal, L., et al., "Growth Factors: Regulation of Normal and Neoplastic Growth", J. of Pathology, vol. 169, pp 191–201, 1993.

Ratner, L., et al., "Complete nucleotide sequence of the AIDS virus, HTLV–III", Nature, vol. 313, pp. 277–284, 1985.

Rehemtulla, A., et al., "High Level Expression of Recombinant Human Tissue Factor in Chinese Hamster Ovary Cells as a Human Thromboplastin", Thromb. and Haemo., vol. 65, pp. 521–527, 1991.

Robinson, H.L., et al., "Protection against a lethal influenza virus challenge by immunization with a haemagglutinin–expressing plasmid DNA", Vaccine, vol. 11, Issue 9, pp. 957–960, 1993.

Schaible, U.E., et al., "Distinct patterns of protective antibodies are generated against *Borrelia burgdorferi* in mice experimentally inoculated with high and low doses of antigen", Immunology Letters, vol. 36, pp. 219–226, 1993.

Scarpati, E.M., et al., "Human Tissue Factor: cDNA Sequence and Chromosome Localization of the Gene", Biochemistry, vol. 26, pp. 5234–5238, 1987.

Schrewe, H., et al., "Cloning of the Complete Gene for Carcinoembryonic Antigen: Analysis of Its Promoter Indicates a Region Conveying Cell Type–Specific Expression", Molecular and Cellular Biology, pp. 2738–2748, 1990.

Selvaraj, P., et al., "The major Fc receptor in blood has a phosphatidylinositol anchor and is deficient in paroxysmal nocturnal haemoglobinuria", Nature, vol. 333, pp. 565–567, 1988.

Semenza, G.L., et al., "Hypoxia–inducible nuclear factors bind to an enhancer element located 3' to the human erythropoietin gene," Proc. Natl. Acad. Sci, USA, vol. 88, pp. 5680–5684, 1991.

Shipley, J.M., et al., "The Role of Glycosylation and Phosphorylation in the Expression of Active Human β–Glucuronidase", J. of Biological Chemistry, vol. 268, No. 16, pp. 12193–12198, 1993.

Simpson, S.C., et al., "CD4 and p56$^{lck}$ can stably associate when co–expressed in NIH3T3 cells", Oncogene, vol. 4, pp. 1141–1143, 1989.

Spicer, E.K., et al., "Isolation of cDNA clones coding for human tissue factor: Primary structure of the protein and cDNA", Proc. Natl. Acad. Sci, USA, vol. 84, pp. 5148–5152, 1987.

Taniguchi, T., et al., "Structure and expression of a cloned cDNA for human interleukin–2", Nature, vol. 302, pp. 305–310, 1983.

Terman, et al., "Identification of the KDR Tyrosine Kinase As A Receptor For Vascular Endothelial Cell Growth Factor", Biochem. and Biophy. Res. Comm., vol. 187, No. 3, pp. 1579–1586, 1992.

Tiley, L.S., et al., "Conserved Functional Organization of the Human Immunodeficiency Virus Type 1 and Visna Virus Rev Proteins", J. of Virology, vol. 65, No. 7, pp. 3877–3881, 1991.

Tindle, R.W., et al., "Immune Response to Human Papillomaviruses and the Prospects for Human Papillomavirus–Specific Immunisation", Curr. Topics in Microbiol. and Immum., vol. 186, pp. 218–253, 1994.

Triezenberg, S.J., "Structure and function of transcriptional activation domains", Current Opinion in Genetics and Development, vol. 5, pp. 190–196, 1995.

Triezenberg, S.J., et al., "Functional dissection of VP16, the trans–activator of herpes simplex virus immediate early gene expression", Genes & Development, vol. 2, pp. 718–729, 1988.

Turner, J.M., et al., "Interaction of the Unique N–Terminal Region of Tyrosine Kinase p56$^{lck}$ with Cytoplasmic Domains of CD4 and CD8 Is Mediated by Cysteine Motifs", Cell, vol. 60, pp. 755–765, 1990.

Ulmer, J.B., et al., "Heterologous Protection Against Influenza by Injection of DNA Encoding a Viral Protein", Science, vol. 259, pp. 1745–1749, 1993.

Valenzuela, P., et al., "Nucleotide sequence of the gene coding for the major protein of hepatitis B virus surface antigen", Nature, vol. 280, pp. 815–819, 1979.

Venkatesh, L.K., et al., "Mutants in a Conserved Region near the Carboxy–Terminus of HIV–1 Rev Identify Functionally Important Residues and Exhibit a Dominant Negative Phenotype", Virology, vol. 178, pp. 327–330, 1990.

Vijaya, S., et al., "Transport to the Cell Surface of a Peptide Sequence Attached to the Truncated C Terminus of an N–terminally Anchored Integral Membrane Protein", Molecular and Cellular Biology, vol. 8, No. 4, pp. 1709–1714, 1988.

Wang, B., et al., "Gene inoculation generates immune responses against human immunodeficiency virus type 1", Proc. Natl. Acad. Sci. USA, vol. 90, pp. 4156–4160, 1993.

Westerwink, M.A.J., et al., "Anti–idiotypic antibodies as vaccines against carbohydrate antigens", Springer Semin Immunopathol., vol. 15, pp. 227–234, 1993.

Wen, W., et al., "Identification of a Signal for Rapid Export of Proteins from the Nucleus", Cell, vol. 82, pp. 463–473, 1995.

Wen, W., et al., "Heat–stable Inhibitors of cAMP–dependent Protein Kinase Carry a Nuclear Export Signal*", J. of Biological Chemistry, vol. 269, No. 51, pp. 32214–32220, 1994.

Winter, G., et al., "Man–made antibodies", Nature, vol. 349, pp. 293–299, 1991.

Wong, G.G., et al., "Human GM–CSF: Molecular Cloning of the Complementary DNA and Purification of the Natural and Recombinant Proteins", Science, vol. 228, pp. 810–815, 1985.

Xiong, Y., et al., "Human D–Type Cyclin", Cell, vol. 65, pp. 691–699, 1991.

Zapp, M.L., et al., "Sequence–specific RNA binding by the HIV–1 Rev protein", Nature, vol. 342 pp. 714–716, 1989.

Zwicker, J., et al., "Cell cycle regulation of the cyclin A, cds25C and cdc2 genes is based on a common mechanism of transcriptional repression", EMBO J., vol. 14, No. 18, pp. 4514–4522, 1995.

Zwicker, J., et al., "Cell cycle regulation of cdc25C transcription is mediated by the periodic repression of the glutamine–rich activators NF–Y and SP1", Nuc. Acids Res., vol. 23, pp. 3822–3830 1995.

Albert, M.J., et al., "Cultivation and Characterization of Human Rotaviruses with 'Super Short' RNA Patterns", J. of Clinical Microbiology, vol. 25, No. 1, pp. 183–185, 1987.

Alberti, S., et al., "C1q Binding and Activation of the Complement Classical Pathway by *Klebsiella pneumoniae* Outer Membrane Proteins", Infection and Immunity, vol. 61, No. 3, pp. 852–860, 1993.

Anderson, E.L., et al., "Evaluation of Rhesus Rotavirus Vaccine (MMU I8006 in Infants and Young Children", J. of Infectious Diseases, vol. 153, No. 5, pp. 823–831, 1986.

Augustin–Voss, H.G., et al., "Migrating Endothelial Cells Are Distinctly Hyperglycosylated and Express Specific Migration–associated Cell Surface Glycoproteins", J. of Cell Biology, vol. 119, No. 2, pp. 483–491, 1992.

Auron, P.E., et al., "Nucleotide sequence of human monocyte interleukin 1 precursor cDNA", Proc. Natl. Acad. Sci. USA, vol. 81, pp. 7907–7911, 1984.

Battaglia M., et al., "Human Enteric Coronaviruses: Further Characterization and Immunoblotting of Viral Proteins", J. of Infectious Diseases, vol. 155, No. 1, pp. 140–143, 1987.

Berling, B.B., et al., "Cloning of a Carcinoembryonic Antigen Gene Family Member Expressed in Leukocytes of Chronic Myeloid Leukemia Patients and Bone Marrow", Cancer Research, vol. 50, pp. 6534–6539, 1990.

Bensi, G., et al., "Human interleukin–1 beta gene", Gene, vol. 52, pp. 95–101, 1987.

Bellinger–Kawahara, C., et al., "Complement Component C3 Fixes Selectively to the Major Outer Membrane Protein (MOMP of *Legionella pneumophila* and Mediates Phagocytosis of Liposome–MOMP Complexes by Human Monocytes", J. Exp. Med., vol. 172 pp. 1201–1210, 1990.

Blaser, M.J., "*Helicobacter pylori* and the Pathogenesis of Gastroduodenal Inflammation" J. of Infectious Diseases, pp. 626–633, 1990.

Bogerd, H.P., et al., "Identification of a Novel Cellular Cofactor for the Rev/Rex Class of Retroviral Regulatory Proteins", Cell, vol. 82, pp. 485–494, 1995.

Brent, R., et al., "A Eukaroytic Transcriptional Activator Bearing the DNA Specificity of a Prokaryotic Repressor", Cell, vol. 43, pp. 729–736, 1985.

Brent, R., et al., "A bacterial repressor protein or a yeast transcriptional terminator can block upstream activation of a yeast gene", Nature, vol. 312, pp. 612–615, 1984.

Brown, D.J., et al., "Redundancy of Signal and Anchor Functions in the $NH_2$–Terminal Uncharged Region of Influenza Virus Neuraminidase, a Class II Membrane Glycoprotein", J. of Virology, pp. 3824–3831, 1988.

Campo, R.E., et al., "M Proteins of Group G Streptococci: Mechanisms of Resistance to Phagocytosis", J. of Infectious Diseases, vol. 171, pp. 601–606, 1995.

Cerny, A., et al., "The Class 1–Restricted Cytotoxic T Lymphocyte Response to Predetermined Epitopes in the Hepatitis B and C Viruses", Microbiol. and Immun., vol. 189, pp. 169–186, 1994.

Chanock, S.J., et al., "Human Rotaviruses and Genome RNA", J. of Infectious Diseases, vol. 148, No. 1, pp. 49–50, 1983.

Chasman, D.I., et al., "GAL4 Protein: Purification, Association with GAL80 Protein, and Conserved Domain Structure", Molecular and Cellular Biology, vol. 10, No. 6, pp. 2916–2923, 1990.

Christoffersen, R.E., et al., "Ribozymes as Human Therapeutic Agents", J. of Medical Chemistry, vol. 38, No. 12, pp. 2023–2037, 1995.

Clark, et al., "Genomic sequence for human prointerleukin 1 beta: possible evolution from a reverse transcribed prointerleukin 1 alpha gene", Nuc. Acids Res., vol. 14, No. 20, pp. 7897–7914, 1986.

Clissold, P.M., "A cDNA construct of tissue inhibitor of metalloproteinases (TIMP linked to the last exon of Thy–1 confers glycophospholipid anchorage on this naturally secreted protein", Biochem. Journal, vol. 281, pp. 129–136, 1992.

Cochrane, A.W., et al., "Identification of Sequences Important in the Nucleolar Localization of Human Immunodeficiency Virus Rev: Relevance of Nucleolar Localization to Function", J. of Virology, vol. 64, No. 2, pp. 881–885, 1990.

Fischer, U., et al., "The HIV–1 Rev Activation Domain Is a Nuclear Export Signal That Accesses an Export Pathway Used by Specific Cellular RNAs", Cell, vol. 82, pp. 475–483, 1995.

Fleckenstein, B., et al., "Tumour induction with DNA of oncogenic primate herpesviruses", Nature, vol. 274, pp. 57–59, 1978.

Flehmig, B., "Hepatitis A", Bailliere's Clinical Gastroenterology, vol. 4, No. 3, pp. 707–720, 1990.

Fischer, U., "Evidence that HIV–1 Rev directly promotes the nuclear export of unspliced RNA", EMBO Journal, vol. 13, No. 17, pp. 4105–4112, 1994.

Fletcher, M., et al., "Recent Advances in the Understanding of the Biochemistry and Clinical Pharmacology of Interleukin–2", Lymphokine Research, vol. 6, No. 1, pp. 45–57, 1987.

Fritzinger, D.C., et al., "Molecular cloning and derived primary structure of cobra venom factor", Proc. Natl. Acad. Sci. USA, vol. 91, pp. 12775–12779, 1994.

Furutani, Y., et al., "Complete nucleotide sequence of the gene for human interleukin 1 alpha", Nuc. Acids Res., vol. 14, No. 8, pp. 3167–3179, 1986.

Galdiero, F., et al., "Activation of Complement System by Porins Extracted from *Salmonella typhimurium*", Infection and Immunity, vol. 46, No. 2, pp. 559–563, 1984.

Pizzo, P.A., et al., "Perspectives on Pediatric Human Immunodeficiency Virus Infections", Pediatric Infect. Dis. J., vol. 10, No. 9, pp. 684–695, 1991.

Givol, D., "The Minimal Antigen–Binding Fragment of Antibodies—Fv Fragment", Molecular Immunology, vol. 28, No. 12, pp. 1379–1386, 1991.

Glass, R.I., et al., "Rotavirus Vaccines: Success by Reassortment", Science, vol. 265, pp. 1389–1391, 1994.

Gough, N.M., et al., "Molecular cloning of cDNA encoding a murine haematopoietic growth regulator, granulocyte–macrophage colony stimulating factor", Nature, vol. 309, pp. 763–767, 1984.

Guddat, U., et al., "Protein–Mediated Nuclear Export of RNA: 5S rRNA Containing Small RNPs in Xenopus Oocytes", Cell, vol. 60, pp. 619–628, 1990.

Hall, C.B., "Prospects for a Respiratory Syncytial Virus Vaccine", Science, vol., 265 pp. 1393–1394, 1994.

Hawkins, R.E., et al., "A Genetic Approach to Idiotypic Vaccination", J. of Immunotherapy, vol. 14, pp. 273–278, 1993.

Heermann, K.H., et al., "Large Surface Proteins of Hepatitis B Virus Containing the Pre–s Sequence", J. of Virology, vol. 52, No. 2, pp. 396–402, 1984.

Henderson, B., et al., "Modulins: A new class of cytokine–inducing, pro–inflammatory bacterial virulence factor", Inflamm., Res. vol. 44, pp. 187–197, 1995.

Herber, B., et al., "Inducible regulatory elements in the human cyclin D1 promoter", Oncogene, vol. 9, pp. 1295–1304, 1994.

Hetherington, S.V., et al., "Complement Component 3 Binding to *Haemophilus influenzae* Type b in the Presence of Anticapsular and Anti–Outer Membrane Antibodies", Inf. and Immun., vol. 60, No. 1, pp. 19–24, 1992.

Honn, K.V., et al., "Adhesion molecules and tumor cell interaction with endothelium and subendothelial matrix", Cancer and Metastasis Reviews, vol. 11, pp. 353–375, 1992.

Hoogenboom, H.R., et al., "Building Antibodies from their genes", Rev. Fr. Transfus. Hemobiol., vol. 36, pp. 19–47, 1993.

Hsiao, K.M., et al., "Multiple DNA elements are required for the growth regulation of the mouse E2F1 promoter", Genes & Development, vol. 8, pp. 1526–1537, 1994.

Huang, J., et al., "A Novel Hepatitis B Virus (HBV) Genetic Element with Rev Response Element–Like Properties That Is Essential for Expression of HBV Gene Products", Molecular and Cellular Biology, vol. 13, No. 1, pp. 7476–7486, 1993.

Hughes, B.J., et al., "Monoclonal Antibody Targeting of Liposomes to Mouse Lung in Vivo" Cancer Research, vol. 49, pp. 6214–6220, 1989.

Huston, J.S., et al., "Medical Applications of Single–Chain Antibodies", Intern. Rev. Immunol., vol. 10, pp. 195–217, 1993.

Iwai, S., et al., "Recognition of the high affinity binding site in rev–response element RNA by the Human Immunodeficiency Virus type–1 rev protein", Nuc. Acids Res., vol. 20, No. 24, pp. 6465–6472, 1992.

Iwarson, S., "The Main Five Types of Viral Hepatitis: An Alphabetical Update", Scand. J. Infect. Dis., vol. 24, pp. 129–135, 1992.

Jacob, L., et al., "Potential therapeutic applications of magainins and other antimicrobial agents of animal origin", Antimicrobial Peptides, pp. 197–223, 1994.

Johnson, D.G., et al., "Autoregulatory control of E2F1 expression in response to positive and negative regulators of cell cycle progression", Genes & Development, vol.8, pp. 1514–1525, 1994.

Jung, M.–C., et al., "T cell recognition of hepatitis B and C viral antigens", European J. of Clinical Investigation, vol. 24, pp. 641–650, 1994.

Kim, B., et al., "Dimerization of a Specific DNA–Binding Protein on the DNA", Science, vol. 255, pp. 203–206, 1992.

Katz, S.L., et al., "Measles Vaccine: Do We Need New Vaccines or New Programs?", Science, vol. 265, pp. 1391–1392, 1994.

Kinchington, P.R., et al., "The Glycoprotein Products of Varicella–Zoster Virus Gene 14 and Their Defective Accumulation in a Vaccine Strain (Oka)", J. of Vir., vol. 64, No. 9, pp. 4540–4548, 1990.

Kjems, J., et al., "Structural analysis of the interaction between the human immunodeficiency virus Rev protein and the Rev response element", Proc. Natl. Acad. Sci. USA, pp. 683–687, 1991.

Kjems, J., et al., "Specific binding of a basic peptide from HIV–1 Rev", EMBO Journal, vol. 11, No. 3, pp. 1119–1129, 1992.

Knapp, B., et al., "Protection of Aotus Monkeys from Malaria Infection by Immunization with Recombinant Hybrid Proteins", Infection and Immunity, vol. 60, No. 6, pp. 2397–2401, 1992.

Koff, A., et al., "Human Cyclin E, a New Cyclin That Interacts with Two Members of the CDC2 Gene Family", Cell, vol. 66, pp. 1217–1228, 1991.

Kozak, M., "The Scanning Model for Translation: An Update", J. of Cell Biology, vol. 108, pp. 229–241, 1989.

Collier, A.C., et al., "Cervical but Not Urinary Excretion of Cytomegalovirus Is Related to Sexual Activity and Contraceptive Practices in Sexually Active Women", J. of Infectious Diseases, vol. 171, pp. 33–38, 1995.

Consolo, F., et al., "Nosography and Immunopathogenesis of Viral Hepatitis", Nephron, vol. 61, pp. 251–254, 1992.

Cosman, D., et al., "Human Macrophage Colony Stimulating Factor (M–CSF): Alternate RNA Splicing Generates Three Different Proteins that are Expressed on the Cell Surface and Secreted", Behring Inst. Mitt., No. 83, pp. 15–26, 1988.

Cover, T.L., et al., "Characterization of and Human Serologic Response to Proteins in *Helicobacter pylori* Broth Culture Supernatants with Vacuolizing Cytotoxin Activity", Infection and Immunity, vol. 58, No. 3, pp. 603–610, 1990.

Cover, T.L., et al., "Purification and Characterization of the Vacuolating Toxin from *Helicobacter pylori*\*", J. of Biological Chemistry, vol. 267, No. 15, pp. 10570–10575, 1992.

Crabtree, J.E., et al., "Mucosal IgA recognition of *Helicobacter pylori* 120 kDa protein, peptic ulceration, and gastric pathology", The Lancet, vol. 338, pp. 332–334, 1991.

Cullen, B.R., "Mechanism of Action of Regulatory Proteins Encoded by Complex Retroviruses", Microbiological Reviews, vol. 56, No. 3, pp. 375–394, 1992.

Cunningham, B.A., et al., "Neural Cell Adhesion Molecule: Structure, Immunoglobulin–Like Domains, Cell Surface Modulation, and Alternative RNA Splicing", Science, vol. 236, pp. 799–805, 1987.

D'Hondt, E., "Possible approaches to develop vaccines against hepatitis A", Vaccine, vol. 10, Suppl. 1, pp. S48–S52, 1992.

Daly, T.J., et al., Specific binding of HIV–1 recombinant Rev protein to the Rev–responsive element in vitro, Nature, vol. 342, pp. 816–819, 1989.

De Vries, C., et al., "the fms–Like Tyrosine Kinase, a Receptor for Vascular Endothelial Growth Factor", Science vol. 255, pp. 989–991, 1992.

De Bruijn, M.H.L., et al., "Human complement component C3: cDNA coding sequence and derived primary structure", Proc. Natl. Acad. Sci. USA, vol. 82, pp. 708–712, 1985.

Deonarain, M.P., et al., "Targeting enzymes for cancer therapy: old enzymes in new roles", Br. J. Cancer, vol. 70 pp. 786–794, 1994.

Dingwall, C., et al., "Nuclear targeting sequences—a consensus", TIBS, vol. 16, pp. 478–481 1991.

Du, R–P., et al., "A Prototype Recombinant Vaccine Against Respiratory Syncytial Virus and Parainfluenza Virus Type 3", Bio/Technology, vol. 12, pp. 813–818, 1994.

Dunn, B.E., et al., "Identification and Purification of a cpn60 Heat Shock Protein Homolog from *Helicobactaer pylori*", Infection and Immunity, vol. 60, No. 5, pp. 1946–1951, 1992.

Dunn, B.E., et al., "Purification and Characterization of Urease from *Helicobacter pylori*", J. of Biological Chemistry, vol. 265, No. 16, vol. 265, pp. 9464–9469, 1990.

Dyall–Smith, M.L., et al., "Gene–Coding Assignments of Rotavirus Double–Stranded RNA Segments 10 and 11", J. of Virology, vol. 38, No. 3, pp. 1099–1103, 1981.

Emerman, M., et al., "The rev Gene Product of the Human Immunodeficiency Virus Affects Envelope–Specific RNA Localization", Cell, vol. 57, pp. 1155–1165, 1989.

Enders, B., et al., "Strategies for the development of an antimalarial vaccine", Vaccine, vol. 10, Issue 13, pp. 920–927, 1992.

Espersen, F., "Complement Activation By Clumping Factor and Protein A From *Staphylococcus aureus* Strain E 2371", Acta path. microbiol. immunol. scand. Sect. C, vol. 93, pp. 59–64, 1985.

Esteban, J.I., et al., "Hepatitis C: Molecular Biology, Pathogenesis, Epidemiology, Clinical Features, and Prevention", Progress in Liver Diseases, pp. 253–283.

Fantozzi, D.A., et al., "Thermostable Inhibitor of cAMP–dependent Protein Kinase Enhances the Rate of Export of the Kinase Catalytic Subunit from the Nucleus\*", J. of Biological Chemistry, vol. 269, No. 4, pp. 2676–2686, 1994.

Felber, B.K., et al., "rev protein of human immunodeficiency virus type 1 affects the stability and transport of the viral mRNA", Proc. Natl. Acad. Sci. USA, vol. 86, pp. 1495–1499, 1989.

Fenton, M.J., "Review: Transcriptional and Post–Transcriptional Regulation of Interleukin 1 Gene Expression", Int. J. Immunopharmac., vol. 14, No. 3, pp. 401–411, 1992.

Ferguson, M.A.J., "Cell–Surface Anchoring of Proteins Via Glycosyl–Phosphatidylinositol Structures", Ann. Rev. Biochem., vol. 57, pp. 285–320, 1988.

Letter from Dale A. Matthews, M.D. et al. University of Connecticut Health Center, Letter and Corrections. p. 512.

\* cited by examiner

Activator-responsive promoter unit

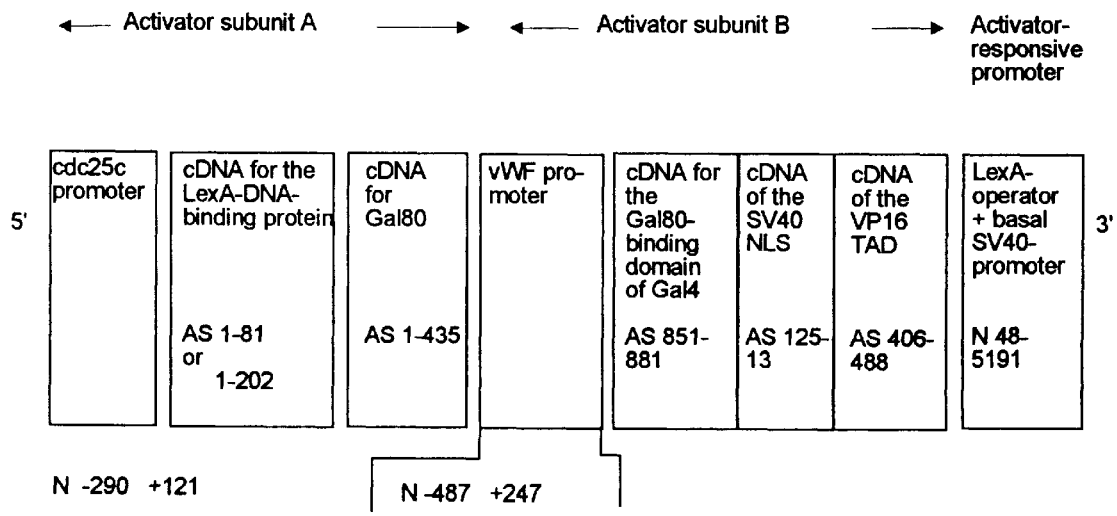

(N = Nucleotide sequence; AS = Amino acid sequence)

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

AGCTTCCGCA TGCTGATGAG GCCGCAAGGC CGAAACGGCA G      41

(2) INFORMATION FOR SEQ ID NO: 2:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

AATTCTGCCG TTTCGGCCTT GCGGCCTCAT CAGCATGCGG A          41

(2) INFORMATION FOR SEQ ID NO: 3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

AGCTTCCAGC CTGATGAGGC CGCAAGGCCG AAACAGGAAG          40

(2) INFORMATION FOR SEQ ID NO: 4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

AATTCTTCCT GTTTCGGCCT TGCGGCCTCA TCAGGCTGGA          40

(2) INFORMATION FOR SEQ ID NO: 5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AGCTTGCACA CTGATGAGGC CGCAAGGCCG AAACTGCG          38

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AATTCGCAGT TTCGGCCTTG CGGCCTCATC AGTGTGCA          38

(2) INFORMATION FOR SEQ ID NO: 7:

(i) SEQUENCE CHARACTERISTICS:

-continued

```
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

AGCTTGAAGT TTATACTGAT GAGGCCGCAA GGCCGAAACT TCAG                    44

(2) INFORMATION FOR SEQ ID NO: 8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

AATTCTGAAG TTTCGGCCTT GCGGCCTCAT CAGTATAAAC TTCA                    44

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

TACTGTATGT ACATACAGTA                                               20

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CGGACAATGT TGACCG                                                   16

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 11:

Pro Lys Lys Lys Arg Lys Val
1               5
```

NUCLEIC ACID CONSTRUCTS CONTAINING GENES ENCODING TRANSPORT SIGNALS

FIELD

The present application relates to nucleic acid constructs containing genes encoding transport signals, which can be used to manipulate the retention of transcription products in a cell's nucleus.

BACKGROUND

In gene therapy, genes are introduced into an organism for the purpose of expressing them in the organism. The regulation of the expression of these genes is important to the prophylactic or therapeutic effect of gene therapy.

Patent Applications PCT/GB95/02000, PCT/EP95/03370, PCT/EP95/03371, PCT/EP95/03368, PCT/EP95/03339 describe gene expression regulators. These regulators comprise an activator sequence whose function is, for example, the cell-specific or virus-specific activation of basal transcription. The DNA sequence of this activator sequence is linked, by its 3' end, to the 5' end of a promoter module. The structural gene is in turn linked, by its 5' end, to the 3' end of the promoter module.

The promoter module comprises nucleic acid sequences which bind to the transcription factors of the CDF and CHF or E2F and CHF families. In the G0 and G1 phases of the cell cycle, this binding leads to inhibition of the upstream activator sequence and consequently to inhibition of the transcription of the structural gene which is located downstream (i.e., in the direction of transcription).

In the G0 and G1 phases of cell division, the DNA contained in the cell is in the diploid state. The cell is at rest in the G0 phase and is inhibited in its cell-cycle progression in the G1 phase. The G1 phase is followed by the S phase, in which DNA synthesis takes place and in which the genome is replicated. There then follows the G2 phase, in which the cell is in the tetraploid state. The G2 phase is followed by cell division (mitosis or "M phase"). The daughter cells pass into the G0 or G1 states, and so on.

Consequently, combining a cell-specific or virus-specific activator sequence with a promoter module which inhibits this activator sequence in the G0 and G1 phases makes it possible to regulate the expression of a structural gene both in a cell-specific or virus-specific manner and in a cell-cycle-specific manner (i.e., restricted to the S and G2 phases).

The combination of an activator sequence and a promoter module is termed a "chimeric" promoter. While there are numerous possibilities for applying chimeric promoters in gene therapy, the shortcomings of these promoters also impose a number of limitations.

Examples of these limitations include:
- a weak activator sequence, which leads to insufficient transcription of the structural gene,
- the use of an activator sequence which cannot be adequately inhibited in a cell-cycle-dependent manner by the chosen promoter module,
- the restriction to two (for example cell or virus-specific and cell-cycle-specific) regulators of the transcription of the structural gene, and
- inadequate retention of the transcription product in the cell nucleus
- and/or inadequate intracellular transport of the transcription product of the structural gene which has been introduced into the cell.

SUMMARY

It is an object of the present invention to make available nucleic acid constructs which make it possible to regulate the expression of foreign genes (transgenes) in a host cell in a more precise manner. The present invention relates, therefore, to nucleic acid constructs which possess a gene encoding a nuclear retention signal which is linked, downstream in the reading direction, to a transgene.

BRIEF DESCRIPTION OF THE DRAWINGS

FIG. 13 is a diagram of the components of another nucleic acid construct of the present invention.

FIG. 14 is a diagram of the components of another nucleic acid construct of the present invention.

DETAILED DESCRIPTION

Figure 1:
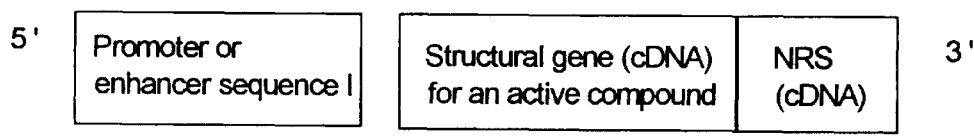
FIG. 1 is a diagram of the components of a nucleic acid construct of the present invention.

Preferably, the nucleic acid constructs of the invention comprise at least the following components, arranged in order of the reading direction from the 5' end to the 3' end:
  a) a first nonspecific, cell-specific, virus-specific, metabolically and/or cell-cycle-specifically activatable promoter sequence or enhancer sequence (I) which activates the basal transcription of a transgene,
  b) a transgene, which is preferably a structural gene encoding a therapeutically active compound, and
  c) a nuclear retention signal whose cDNA is linked, directly or indirectly, by its 5' end to the 3' end of the structural gene (b).

Preferably, the transcription product of the nuclear retention signal has a structure which binds to a nuclear export factor.

The novel nucleic acid constructs optionally may include the following components in addition to components a) to c):

d) a second promoter sequence or enhancer sequence (II) which activates the basal transcription of a nuclear export factor, and e) a nucleic acid which encodes a nuclear export factor which binds to the transcription product of the nuclear retention signal (c) and thereby mediates transport of the transcription product of the transgene out of the cell nucleus.

The first (I) promoter sequence or enhancer sequence (a) and the second (II) promoter sequence or enhancer sequence (d) can be identical to one another or different from each other within a given construct. Preferably, at least one of the components a) and d) is nonspecifically, cell-specifically, virus-specifically, metabolically, or cell-cycle-specifically activatable. In the case of a metabolically activatable component a) or d), the mode of activation is by hypoxia.

Preferably, at least one of the promoter sequences or enhancer sequences (a) and (d) is a chimeric promoter in which a promoter module, e.g., CDE-CHR or E2FBS-CHR, interacts with an adjacent upstream cell-specifically, virus-specifically or metabolically activatable activator sequence and can thereby influence, in particular inhibit, the expression of a downstream gene.

In another embodiment, the components a) and d) can be an activator-responsive promoter unit. Constructs of this embodiment additionally include the following components:

f) at least a third promoter sequence or enhancer sequence which is nonspecifically, virus-specifically, metabolically or cell-specifically and/or cell-cycle-specifically activatable, g) at least one activator subunit which is located downstream of the promoter sequence or enhancer sequence (f) and is activated, in its basal transcription, by the promoter sequence or enhancer sequence (f), and h) an activator-responsive promoter which is activated by the expression products of one or more of activator subunit(s) (g).

In a preferred embodiment, the nucleic acid constructs are nucleic acid constructs in which the promoter sequence or enhancer sequence (a) and/or (d) and/or the activator-responsive promoter is a chimeric promoter and the activator subunit (g) is a at least one gene encoding at least one transcription factor which activates the chimeric promoter of the activator-responsive promoter (h).

The LexA operator in combination with the SV40 promoter is an example of an activator-responsive promoter (h) which is activated by two activator subunits (g, g'). The activator subunit (g) comprises the cDNA for the LexA DNA-binding protein, preferably encoding amino acids 1–81 or 1–202 of the LexA DNA-binding protein, whose 3' end is linked to the 5' end of the cDNA for the Gal80 protein (which preferably encodes amino acids 1–435 of the Gal80 protein). The second activator subunit (g') comprises the cDNA of the Gal80 -binding domain of the Gal4 protein, which preferably encodes amino acids 851–881 of the Gal4 protein, whose 3' end is linked to the 5' end of the cDNA of the SV40 large T antigen preferably encoding amino acids 126–132, whose 3' end is linked to the 5' end of the cDNA for the HSV-1 VP16 transactivating domain preferably encoding amino acids 406–488.

The binding sequence for the Gal4 protein in combination with the SV40 promoter is another example of an activator-responsive promoter which is activated by two activator subunits (g, g'). The activating unit (g) comprises the cDNA for the DNA-binding domain of the Gal4 protein (preferably encoding amino acids 1–147), whose 3' end is linked to the 5' end of the cDNA for the Gal80 protein (preferably encoding amino acids 1–435). The second activating subunit (g') comprises the cDNA for the Gal80 -binding domain of Gal4 (preferably encoding amino acids 851–881), whose 3' end is linked to the 5' end of the cDNA of the nuclear localization signal of SV40 (SV40 large T, preferably encoding amino acids 126–132) whose 3' end is linked to the 5' end of the cDNA for the HSV-1 VP16 transactivating domain (preferably encoding amino acids 406–488).

Another example of two activator subunits (g, g') which activate the activator-responsive promoter which is composed of the binding sequence for the Gal4 protein and the SV40 promoter is represented by an activating unit (g) comprising the cDNA for the cytoplasmic domain of the CD4 T cell antigen (preferably encoding amino acids 397–435), whose 5' end is linked to the 3' end of the cDNA for the HSV-1 VP16 transactivating domain (preferably encoding amino acids 406–488), whose 5' end is in turn linked to the 3' end of the cDNA of the nuclear localization signal of SV40 (preferably SV40 large T nuclear localization signal cDNA encoding amino acids 126–132), and the activating unit (g') comprising the cDNA of the nuclear localization signal of SV40 (preferably SV40 large T nuclear localization signal cDNA encoding amino acids 126–132); whose 3' end is linked to the 5' end of the cDNA for the DNA-binding domain of the Gal4 protein (preferably encoding amino acids 1–147), whose 3' end is linked to the 5' end of the cDNA for the CD4-binding sequence of the p56 lck protein (preferably encoding amino acids 1–71).

Preferably, the gene encoding the nuclear retention signal is selected from the group consisting of the rev-responsive element (RRE) of HIV-1 or HIV-2, the RRE-equivalent retention signal of retroviruses or the RRE-equivalent retention signal of HBV.

The nuclear export factor (e) is preferably a gene selected from the group consisting of the rev gene of the viruses HIV-1, HIV-2, maedi-visna virus, caprine arthritis encephalitis virus, equine infectious anemia virus, feline immunodeficiency virus, of retroviruses, of HTLV or the gene of the hnRNP-A1 protein or the gene of the transcription factor TFIII-A. Preferably, the nucleic acid is DNA. The novel nucleic acid constructs are customarily employed as vectors, in particular plasmid vectors or viral vectors.

Preferably, the transgenes are structural genes which encode a pharmacologically active compound which is preferably selected from the group consisting of cytokines, growth factors, antibodies or antibody fragments, fusion proteins between ligands, such as antibodies or antibody fragments, and cytokines or growth factors, receptors for cytokines or growth factors, proteins having an antiproliferative or cytostatic effect, angiogenesis inhibitors, coagulation factors, thrombosis-inducing substances, coagulation inhibitors, substances having a fibrinolytic effect, complement-activating proteins, virus coat proteins, bacterial antigens, parasitic antigens, proteins having an effect on blood circulation, and ribozymes.

Preferably, the transgene (b) is a structural gene which encodes a ribozyme which inactivates the mRNA which encodes a protein selected from the group consisting of cell-cycle control proteins, in particular cyclin A, cyclin B, cyclin D1, cyclin E, E2F1-5, cdc2, cdc25C and DP1, virus proteins, cytokines, growth factors, and their receptors.

In a preferred embodiment, the transgene is a structural gene which encodes a protein which triggers controlled cell death (apoptosis), in particular sphingomyelinase.

In still another preferred embodiment, the transgene (b) is a structural gene which encodes an enzyme which cleaves a precursor of a drug, thereby forming a drug. With this embodiment, the structural gene may encode a ligand-enzyme fusion protein, with the enzyme cleaving a precursor of a drug, thereby forming a drug, and the ligand binding to a cell surface, preferably to endothelial cells or tumor cells.

The promoter sequence, enhancer sequence or activator sequence is preferably selected from the group consisting of gene-regulatory nucleotide sequences which are activated in endothelial cells, smooth muscle cells, striated muscle cells, macrophages, lymphocytes, tumor cells, liver cells, leukemia cells and glia cells, or selected from the group consisting of promoter sequences of the HBV, HCV, HSV, HPV, EBV, HTLV and HIV viruses.

The invention also relates to isolated cells or cell lines which harbor a novel nucleic acid construct. A host cell transformed with such a nucleic acid construct can be used to prepare a pharmaceutical composition for the treatment of a disease, the preparation of the medicine comprising the introduction of the nucleic acid construct into a target cell. Diseases preferred for treatment with such compositions include those involving excessive cell multiplication (cell proliferative disorders). In order to prepare the medicine, a nucleic acid construct must first of all be introduced into the target cell.

The novel nucleic acid constructs make it possible to use any promoters, enhancers or activator sequences and, in particular, to augment the retention in the cell nucleus of the transcription product of the structural gene which has been introduced into the cell or to increase the intracellular transport of the transcription product of the structural gene which has been introduced into the cell.

The preferred nucleic acid construct for augmented retention of the transcription product in the cell nucleus comprises the following components:
a) a promoter sequence or enhancer sequence I which activates the basal transcription of the structural gene,
b) a transgene (structural gene), which is preferably in the form of a cDNA which encodes a desired therapeutically active compound, and
c) a nuclear retention signal (NRS) whose cDNA is preferably directly linked, at the 5' end, to the 3' end of the structural gene.

The arrangement of the individual components a)–c) is depicted, by way of example, in FIG. 1.

The novel nucleic acid construct for increased intracellular transport of the transcription product preferably includes, in addition to a promoter sequence or enhancer sequence I, which activates the basal transcription of the structural gene, and a transgene, which encodes the desired active compound, a nuclear retention signal (NRS) whose cDNA is linked, at the 5' end, to the 3' end of the structural gene and whose messenger RNA is the structure for binding a nuclear export factor (NEF).

In addition to this, nucleic acid constructs of this embodiment may optionally include a second promoter sequence or enhancer sequence (II), which activates the basal transcription of the cDNA of the nuclear export factor (NEF), and the cDNA encoding a nuclear export factor (NEF), whose expression product binds to the nuclear retention signal (NRS) and thereby mediates transport of the transcription product of the structural gene out of the cell nucleus.

Figure 2:
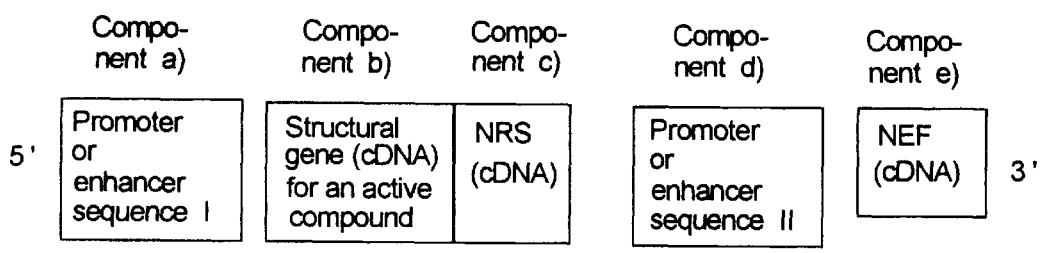
FIG. 2 is a diagram of the components of another nucleic acid construct of the present invention.

The arrangement of the individual components of this embodiment is depicted, by way of example, in FIG. 2.

In the novel nucleic acid constructs, the promoter sequences or enhancer sequences of components a) or d) can be identical with one another or different and, furthermore, components d) and e) can be located upstream or downstream of components a), b) and c).

At least one strong promoter sequence or enhancer sequence, for example, from CMV (EP-A-0173177) or SV40, or any other promoter sequence or enhancer sequence known in the art, is preferably used as a promoter sequence or enhancer sequence.

In a preferred embodiment, at least one promoter sequence or enhancer sequence in the novel nucleic acid constructs is cell-specifically, metabolically (for example by hypoxia), virus-specifically or cell-cycle-specifically activatable.

Especially preferred are:
those promoter sequences or enhancer sequences which activate transcription in endothelial cells, smooth muscle cells, striated muscle cells, hematopoietic cells, lymphocytes, macrophages, glia cells or tumor cells in a cell-specific manner and/or promoter sequences or enhancer sequences of the HBV, HCV, HSV, HPV, CMV, EBV, HTLV or HIV viruses and/or promoter sequences or enhancer sequences which are metabolically activatable, such as the hypoxia-inducible enhancer (Semenza et al., *PNAS* 88, 5680 (1991)) or promoter (McBurney et al., *Nucleic Acids Res.* 19, 5755 (1991); WO 95/21927) and/or promoters which are cell-cycle-specifically activatable, such as the promoter of the cdc25C gene, the cyclin A gene, the cdc2 gene (Lucibello et al., *EMBO J.* 14, 132 (1995), Zwicker et al., *EMBO J.* 14, 4514 (1995), Zwicker et al., Nucl. Acids Res. 23, 2833 (1995)), the B-myb gene (Lam et al., *EMBO J.* 12, 2705 (1993)), the DHFR gene (Means et al., *Mol. Cell Biol.* 12, 1054 (1992) and the E2F-1 gene (Johnson et al., *Genes Dev.* 8, 1514 (1994), Hsiao et al., *Genes Dev.* 8, 15256 (1994)).

In another preferred embodiment, at least one promoter sequence or enhancer sequence in the novel nucleic acid constructs is a chimeric promoter. The chimeric promoter preferably is a combination of an upstream, cell-specifically, metabolically or virus-specifically activatable, activator sequence and a downstream promoter module. The promoter module is characterized by a nucleotide sequence which binds the transcription factors of the CDF and CHF or E2F and CHF families and can thereby inhibit activation of the upstream activator sequence in the G0 and G1 phases of the cell cycle (Lucibello et al., *EMBO J.* 14, 132 (1994), PCT/GB95/02000).

In another preferred embodiment, at least one promoter sequence or enhancer sequence (component a) or d)) in the novel nucleic acid constructs is an activator-responsive promoter unit. An activator-responsive promoter unit is preferably composed of the following components:
f) one or more identical or different promoter sequences or enhancer sequences which is/are, for example, cell-cycle-specifically, metabolically, cell-specifically or virus-specifically activatable or both cell-cycle-specifically and metabolically, cell-specifically or virus-specifically activatable (i.e., chimeric promoters), g) one or more identical or different activator subunits which is/are in each case located downstream of the promoter sequences or enhancer sequences and activated in their basal transcription by these sequences, and h) an activator-responsive promoter which is activated by the expression products of one or more activator subunits.

Figure 3:
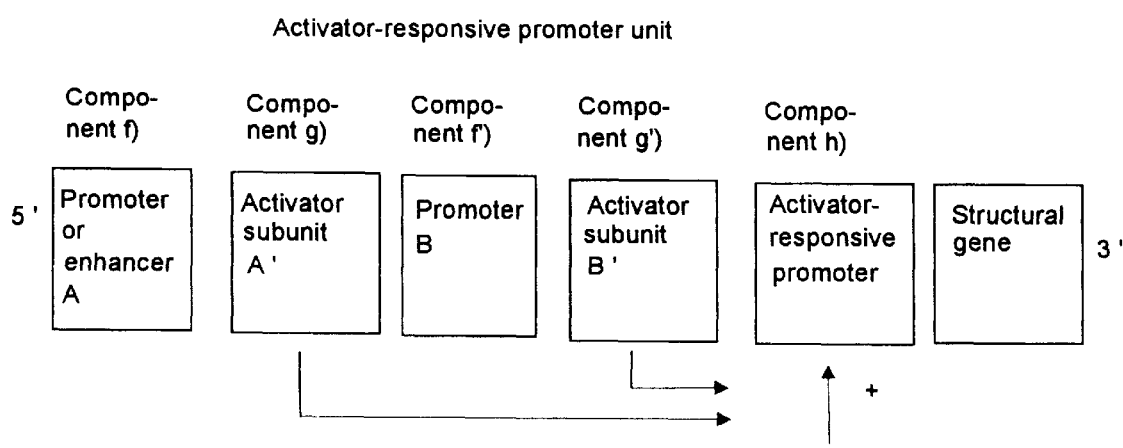
FIG. 3 is a diagram of the components of another nucleic acid construct of the present invention.
Figure 4:
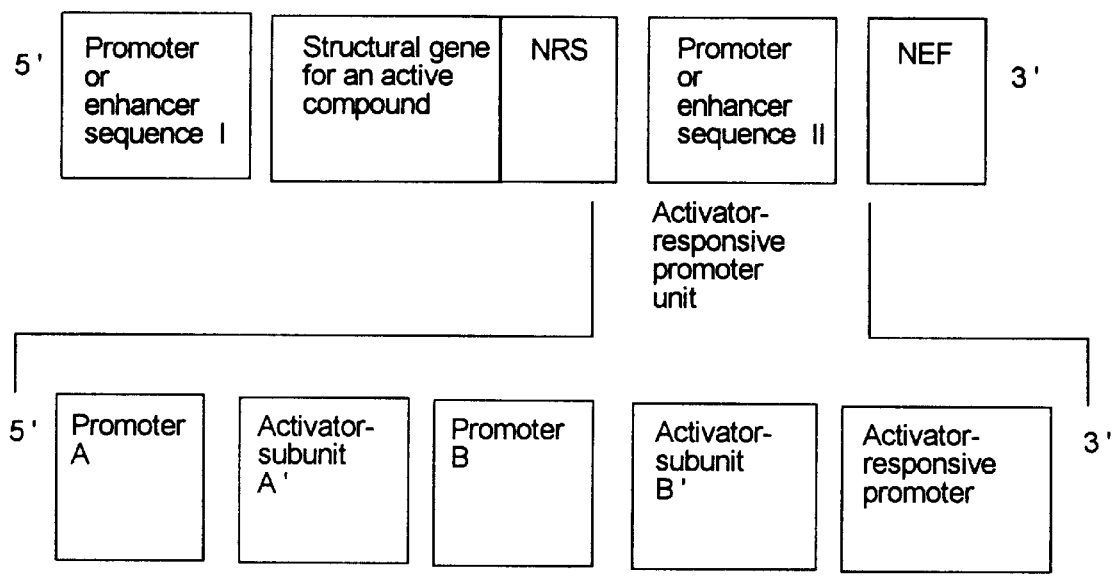
FIG. 4 is a diagram of the components of another nucleic acid construct of the present invention.

The arrangement of the individual components of a preferred activator-responsive promoter unit is depicted by FIG. 3. The insertion of a preferred activator-responsive promoter unit into a novel nucleic acid construct is depicted, for example, by FIG. 4.

Figure 5:
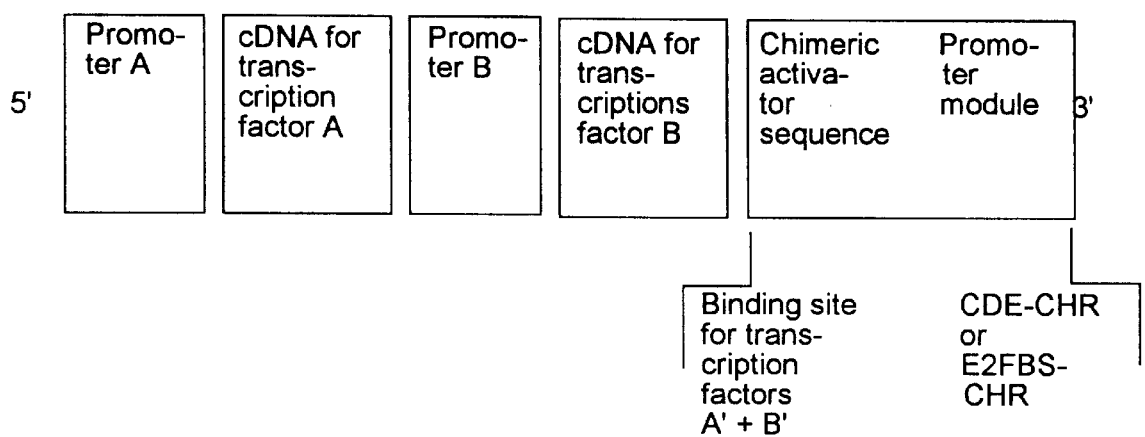
FIG. 5 is a diagram of the components of another nucleic acid construct of the present invention.

In their simplest form, activator-responsive promoter units can, for example, represent chimeric promoter constructs as shown in the diagram in FIG. 5.

In another embodiment, novel activator-responsive promoter units can constitute sequences for binding chimeric transcription factors composed of DNA-binding domains, protein-protein interaction domains and transactivating domains.

Preferred structural genes encoding a pharmacologically active compound are genes for ribozymes, preferably ribozymes having a combined antisense RNA, proteins and glycoproteins which are selected from the group consisting of cytokines, growth factors, receptors for cytokines or growth factors, fusion proteins composed of ligands (e.g., antibodies or antibody fragments) and cytokines or growth factors, proteins having an antiproliferative or cytostatic effect, angiogenesis inhibitors, thrombosis-inducing proteins, blood coagulation inhibitors, complement-activating proteins, coat substances of viruses and coat substances of bacteria.

Particularly preferred as structural genes are genes encoding ribozymes which specifically cleave the mRNA of those genes which encode proteins involved in the control of the cell cycle. These proteins include, in particular, cyclin A, cyclin D1, cyclin E, cyclin B, cdc2, E2F1-5, DP1 and cdc25C (La Thangue, *Current Opin. Cell Biol.* 6, 443 (1994); Mueller, *Trends Genet.* 11, 173 (1995); Zwicker et al., *EMBO J.* 14, 4514 (1995)).

In a preferred embodiment, the nuclear retention signal (NRS) is a nucleotide sequence which, while it impedes transport through the nuclear membrane of a premessenger RNA which is linked to it, is, on the other hand, a structure for binding to an export protein. This export protein mediates transport of the premessenger or messenger RNA which contains an NRS out of the cell nucleus into the cytoplasm. A premessenger or messenger RNA which contains the NRS is consequently secreted from the cell nucleus as a result of binding to the export protein (Fischer et al., *Cell* 82, 475 (1995)).

The NRS is preferably the rev-responsive element (RRE) sequence of retroviruses. In HIV-1, this RRE is a sequence encompassing 243 nucleotides (nucleotides 7362–7595; Muesing et al., *Nature* 313, 450 (1985)) in the env gene (Malim et al., *Nature* 338, 254 (1989); Kjems et al., *PNAS* 88, 683 (1991)). However, within the meaning of the invention, the nuclear retention signal (NRS) can also be a nucleotide sequence which is homologous and/or functionally analogous, such as the RRE-equivalent of HBV virus (Huang et al., *Mol. Cell Biol.* 13, 7476 (1993)).

In the novel nucleic acid constructs, the nuclear export factor (NEF) is a nucleotide sequence which encodes a protein which binds to the mRNA of the NRS and mediates transport of the premessenger RNA or messenger RNA containing an NRS out of the cell nucleus into the cytoplasm (or out of the cytoplasm into the cell nucleus). Preferred is the rev gene from retroviruses, especially from HIV-1 or HIV-2 virus (Daly et al., *Nature* 342, 816 (1989); Emerman et al., *Cell* 57, 1155 (1989); Felber et al., *PNAS* 86, 1495 (1989); Fischer et al., *EMBO J.* 13, 4105 (1994)).

The rev protein of the rev gene of retroviruses binds to the RRE in the pre-mRNA (Iwai et al., *Nucl. Acids Res.* 20, 6465 (1992)) by means of its N-terminal domain (Zapp et al., *Nature* 342, 714 (1989); Malim et al., *Cell* 65, 241 (1991). The bond between the RRE and the rev protein enables "non-spliced" premessenger RNA, and any other RNA which contains an RRE, to be transported from the cell nucleus into the cytoplasm (Fischer et al., *EMBO J.* 13, 4105 (1994); Fischer et al., *Cell* 82, 475 (1995)) and consequently considerably augments translation.

Further included in the invention are nucleotide sequences which encode proteins which are homologous with, or functionally similar to, the rev protein of HIV-1 (Bogerd et al., *Cell* 82, 485 (1995)), such as the rev gene of visna-maedi virus (VMV; Tiley et al., *J. Virol.* 65, 3877 (1991)) or the rev gene of caprine arthritis encephalitis virus (CAEV; Tiley et al., *J. Virol.* 65, 3877 (1991)), which can be used as NEF's.

Genes can also be employed which encode proteins which, while only possessing low or no homology with the rev protein, are nevertheless functionally similar to the rev protein of HIV-1. These genes include, for example, the rex gene of HTLV-1 (Cullen, *Microbiol. Rev.* 56, 375 (1992)), and the rev gene of equine infectious anemia virus (EIAV) and of feline immunodeficiency virus (FIV) (Manusco et al., *J. Virol.* 68, 1988 (1994)).

In an alternative embodiment, the NEF's can also be nucleotide sequences encoding proteins which cause a secretion of RNA from the nucleus even without this RNA being retained in the nucleus by means of an NRS. These proteins include, for example, the transcription factor TFIIIA (Gaddat et al., *Cell* 60, 619 (1990)) or the heterogeneous nuclear ribonucleo-protein A1 (hnRNPA1 protein; Pinol-Roma et al., *Nature* 355, 730 (1992)).

In addition, the nuclear transport proteins include heat shock protein 70 (hsc70 ; Mandell et al., *J. Cell Biol.* 111, 1775 (1990)) and the protein kinase inhibitor CPKI (Fantozzi et al., *J. Biol. Chem.* 269, 2676 (1994), Wen et al., *J. Biol. Chem.* 269, 32214 (1994)).

Features shared by the NEF and its homologous and analogous proteins are a more aminoterminally located domain for binding the monomeric protein to the RNA of the NRS (*J. Virol.* 64, 881 (1990); Kjems et al., *EMBO J.* 11, 1119 (1992)) and a leucine-rich domain (hnRNPA1 is an exception to this) which is required for the transport function of the NEF (Wen et al., *Cell* 82, 463 (1995); Fischer et al., *Cell* 82, 475 (1995); Malim et al., *J. Virol.* 65, 4248 (1991); Venkatesh et al., *J. Virol.* 178, 327 (1990)).

The nucleic acid constructs are preferably composed of DNA. The term nucleic acid constructs is understood to mean artificial nucleic acid structures which can be transcribed in the target cells. They are preferably inserted into a vector, with plasmid vectors or viral vectors being particularly preferred.

Using the novel nucleic acid constructs, a transgene (component b) can be expressed both cell-specifically or virus-specifically or under particular metabolic conditions and also cell-cycle-specifically, with the structural gene preferably being a gene which encodes a pharmacologically active compound or else an enzyme which cleaves an inactive precursor of a drug, thereby forming an active drug. The structural gene can be chosen such that this enzyme is expressed as a fusion protein with a ligand and such that the ligand binds to the surface of cells, for example, proliferating endothelial cells or tumor cells.

The present invention also relates to cells of yeasts or mammals which harbor a novel nucleic acid construct. In a particularly preferred embodiment, the nucleic acid constructs are introduced into cell lines which can then be used, after transfection, for expressing the transgene. These cells can consequently be used as a therapeutic agent for patients and also in the patient and consequently for treating a disease. A preferred use of the novel nucleic acid construct is treating a disease, with the preparation of the pharmaceutical composition comprising the insertion of a nucleic acid construct into a target cell and its virus-specific or target-cell-specific and cell-cycle-specific expression. The disease is frequently a disease which is accompanied by excessive cell multiplication, with the preparation of the medicine comprising the insertion of a nucleic acid construct into a target cell and its virus-specific or target-cell-specific expression during the stage of cell proliferation.

The novel nucleic acid constructs do not occur in nature in this form, i.e., the transgene or structural gene for the active compound or for an enzyme or for a ligand-enzyme fusion protein is not naturally combined with the nuclear retention signal (NRS) and the two are not naturally linked to the promoter I, and this combination, in turn, is not naturally combined with the nucleotide sequence comprising the promoter II and the nuclear export factor (NEF).

The promoters I and II, and the structural gene for the active compound (or for the enzyme), of the novel nucleic acid constructs are selected in accordance with the desired objective.

Figure 6:
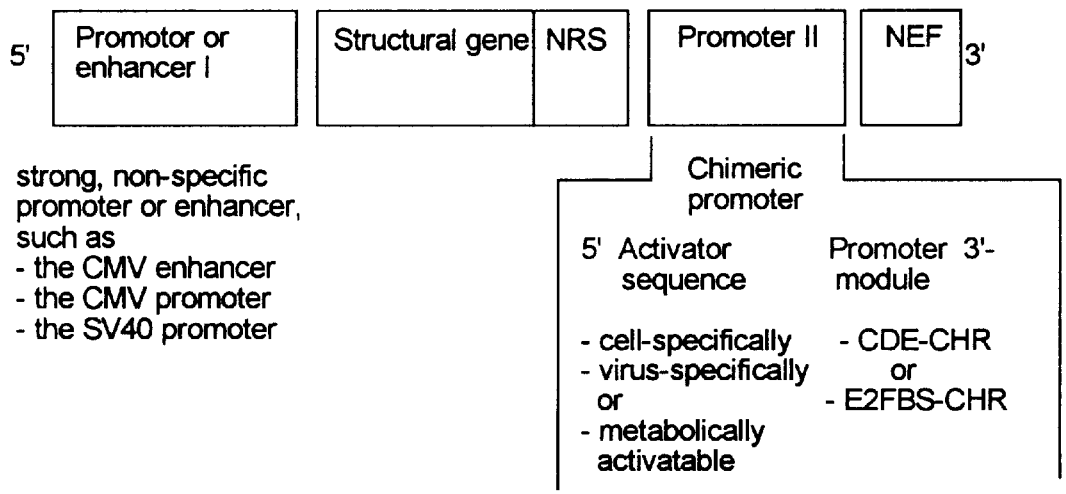
FIG. 6 is a diagram of the components of another nucleic acid construct of the present invention.

Some preferred combinations are presented below:

1.1 Combination of a strong, non-specific promoter or enhancer with a chimeric promoter for expressing a structural gene Examples of such combinations are depicted in FIG. 6.

Figure 7:
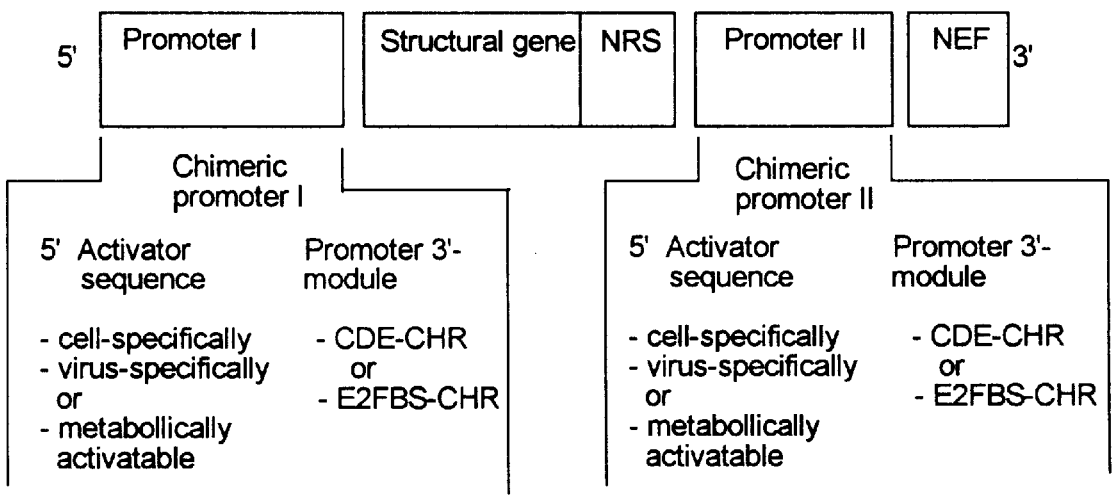
FIG. 7 is a diagram of the components of another nucleic acid construct of the present invention.

1.2 Combination of two different or identical chimeric promoters for expressing a structural gene Examples of such combinations are depicted in FIG. 7.

Figure 8:
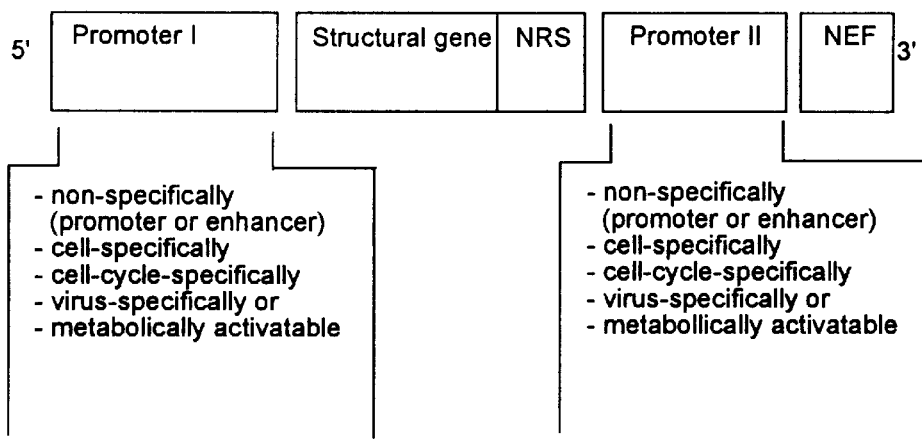
FIG. 8 is a diagram of the components of another nucleic acid construct of the present invention.

1.3 Combination of two different or identical promoters or enhancers for expressing a structural gene Examples of such combinations are depicted in FIG. 8.

1.4 Activator-responsive promoter

Figure 9:
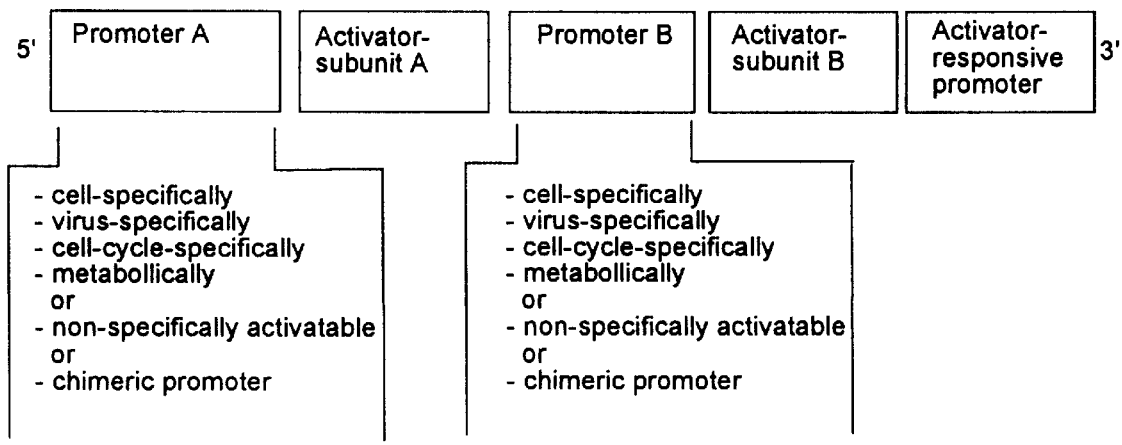
FIG. 9 is a diagram of the components of another nucleic acid construct of the present invention.

Examples of such combinations are depicted in FIG. 9.

Figure 10:
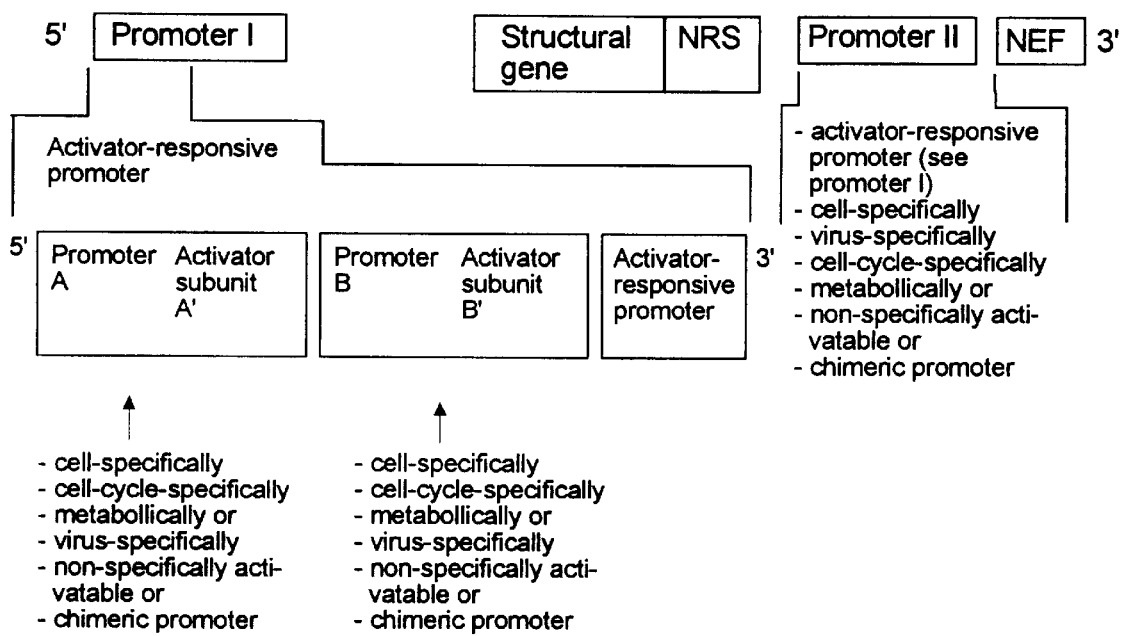
FIG. 10 is a diagram of the components of another nucleic acid construct of the present invention.

1.5 Multiple combination of different promoters for the multiply controlled expression of a structural gene Examples of such combinations are depicted in FIG. 10.

Depending on the planned use of the nucleic acid constructs, the following embodiments can be selected:

2. Therapy of tumors and chronic inflammations by inhibiting the proliferating endothelium 2.1.a) Selection of the promoters or activator sequences which are activated in endothelial cells Preferred promoters or activator sequences composed of promoters or enhancers include those gene-regulatory sequences or elements for genes which encode proteins which can be detected, in particular, in endothelial cells (or else in cells in the immediate vicinity of proliferating endothelial cells). Some of these proteins have been described by Borrows et al. (*Pharmac. Ther.* 64, 155 (1994)) and Plate et al. (*Brain Pathol.* 4, 207 (1994)). Examples of these endothelial-cell-specific proteins are, in particular:

brain-specific, endothelial glucose-1-transporter
  The promoter sequence was described by Murakami et al. (*J. Biol. Chem.* 267, 9300 (1992));
endoglin
  The promoter sequence was described by Bellon et al. (*Eur. J. Immunol.* 23, 2340 (1993)) and Ge et al. (*Gene* 138, 201 (1994));

VEGF-receptors
Two receptors are distinguished (Plate et al., *Int. J. Cancer* 59, 520 (1994)):
  VEGF receptor 1 (flt-1) (de Vries et al., *Science* 255, 989 (1992)) and the
  VEGF receptor 2 (flk-1, KDR) (Terman et al., *BBRC* 187, 1579 (1992)).
Both receptors are almost exclusively found on endothelial cells (Senger et al., *Cancer Metast. Rev.* 12, 303 (1993));
other endothelial-cell-specific receptor tyrosine kinases
  til-1 or til-2 (Partanen et al., *Mol. Cell. Biol.* 12, 1698 (1992), Schnuerch and Risau, *Development* 119, 957 (1993), Dumont et al., *Oncogene* 7, 1471 (1992))
  B61 receptor (Eck receptor) (Bartley et al., *Nature* 368, 558 (1994), Pandey et al., *Science* 268, 567 (1995), van der Geer et al., *Ann. Rev. Cell. Biol.* 10, 251 (1994));
B61
The B61 molecule is the ligand for the B61 receptor. (Holzman et al., *J. Am. Soc. Nephrol.* 4, 466 (1993), Bartley et al., *Nature* 368, 558 (1994));
endothelin, especially
  endothelin B
  The promoter sequence was described by Benatti et al., *J. Clin. Invest.* 91, 1149 (1993).
  endothelin 1
  The promoter sequence was described by Wilson et al., *Mol. Cell. Biol.* 10, 4654 (1990);
endothelin receptors, in particular the endothelin B receptor (Webb et al., *Mol. Pharmacol.* 47, 730 (1995), Haendler et al. *J. Cardiovasc. Pharm.* 20, 1 (1992));
mannose-6-phosphate receptors
The promoter sequences have been described by Ludwig et al. (*Gene* 142, 311 (1994), Oshima et al., (*J. Biol. Chem.* 263, 2553 (1988)) and Pohlmann et al. (*PNAS USA* 84, 5575 (1987));
von Willebrand factor
The promoter sequence was described by Jahroudi and Lynch (*Mol. Cell. Biol.* 14, 999 (1994)), Ferreira et al. (*Biochem. J.* 293, 641 (1993)) and Aird et al. (*PNAS USA* 92, 4567 (1995));
IL-1α and IL-1 β
The promoter sequences were described by von Hangen et al., *Mol. Carcinog.* 2, 68 (1986), Turner et al., *J. Immunol.* 143, 3556 (1989), Fenton et al., *J. Immunol.* 138, 3972 (1987), Bensi et al., *Cell Growth Diff.* 1, 491 (1990), Hiscott et al., *Mol. Cell. Biol.* 13, 6231 (1993) and Mori et al., *Blood* 84, 1688 (1994);
IL-1 receptor
The promoter sequence was described by Ye et al., *PNAS USA* 90, 2295 (1993);
vascular cell adhesion molecule (VCAM-1)
The promoter sequence of VCAM-1 was described by Neish et al., *Mol. Cell. Biol.* 15, 2558 (1995), Ahmad et al., *J. Biol. Chem.* 270, 8976 (1995), Neish et al., *J. Exp. Med.* 176, 1583 (1992), Iademarco et al., *J. Biol. Chem.* 267, 16323 (1992), and Cybulsky et al., *PNAS USA* 88, 7859 (1991); and
synthetic activator sequence
As an alternative to natural endothelium-specific promoters, synthetic activator sequences can also be used which comprise oligomerized binding sites for transcription factors which are preferentially or selectively active in endothelial cells. An example of this is the transcription factor GATA-2, whose binding site in the endothelin-1 gene is 5'-TTATCT-3' (Lee et al., *Biol. Chem.* 266, 16188 (1991), Dorfmann et al., *J. Biol. Chem.* 267, 1279 (1992) and Wilson et al., *Mol. Cell Biol.* 10, 4854 (1990)).

2.1.b) Selection of the promoters or activator sequences which are activated in cells in the vicinity of activated endothelial cells In proliferating endothelia, neighboring cells are accessible, through opened tight junctions, for macromolecules derived from the blood. Because of the functional and anatomical interrelationships, the cells neighboring activated endothelial cells are target cells within the meaning of this invention.

VEGF

The gene-regulatory sequences for the VEGF gene are
  the promoter sequence of the VEGF gene (5' flanking region) (Michenko et al., *Cell. Mol. Biol. Res.* 40, 35 (1994), Tischer et al., *J. Biol. Chem.* 266, 11947 (1991)) or
  the enhancer sequence of the VEGF gene (3' flanking region) (Michenko et al., *Cell Mol. Biol. Res.* 40, 35 (1994)) or
  the c-Src gene (Mukhopadhyay et al., *Nature* 375, 577 (1995), Bonham et al., *Oncogene* 8, 1973 (1993), Parker et al., *Mol. Cell. Biol.* 5, 831 (1985), and Anderson et al., *Mol. Cell. Biol.* 5, 112 (1985)) or
  the V-Scr gene (Mukhodpadhyay et al., *Nature* 375, 577 (1995), Anderson et al., *Mol. Cell. Biol.* 5, 112 (1985) and Gibbs et al., *J. Virol.* 53, 19 (1985));
steroid hormone receptors and their promoter elements (Truss and Beato, *Endocr. Rev.* 14, 459 (1993)), in particular the
  mouse mammary tumor virus promoter The cDNA sequence of the promoter region of the long terminal repeat region of MMTV was described by Chalepakis et al., *Cell* 53, 371 (1988) and Truss and Beato (*Endocr. Rev.* 14, 459 (1993).

2.2. Structural genes for antitumoral or antiinflammatory substances 2.2.a) Inhibitors of proliferation An antitumoral or antiinflammatory substance as used herein is to be understood as being the DNA sequence of a protein which inhibits the proliferation of endothelial cells. Examples of these DNA sequences are those for:
  retinoblastoma protein (pRb/p110) or for its analogs p107 and 120
  p53 protein
  p21 (WAF-1) protein
  p16 protein
  other CdK inhibitors
  GADD45 protein and
  bak protein.

In order to prevent rapid intracellular inactivation of these cell-cycle inhibitors, those genes are preferably to be used which possess mutations for the inactivation sites of the expressed proteins, without the function of these proteins thereby being impaired.

The retinoblastoma protein (pRb) and the related p107 and p130 proteins are inactivated by phosphorylation. Consequently, a pRb/p110 cDNA sequence, p107 cDNA sequence or p130 cDNA sequence is preferably used which is point-mutated in such a way that the phosphorylation sites of the encoded protein are replaced with non-phosphorylatable amino acids.

2.2.b) Coagulation-inducing factors and angiogenesis inhibitors

An antitumoral or antiinflammatory substance also includes the DNA sequence for a protein which induces coagulation and/or inhibits angiogenesis. Examples of these proteins are:
  tissue factor (TF) and coagulation-active fragments thereof (Morrissey et al., *Cell* 50, 129 (1987), Scarpati et al., *Biochem.* 26, 5234 (1987), Spicer et al., *PNAS USA* 84, 5148 (1987), Rehemtulla et al., *Thromb. Heamost.* 65, 521 (1991))
  plasminogen activator inhibitor 1 (PAI-1)
  PAI-2
  PAI-3
  angiostatin
  interferons
    IFNα
    IFNβ
    IFNγ
  platelet factor 4
  IL-12
  TIMP-1
  TIMP-2
  TIMP-3
  leukemia inhibitory factor (LIF).

2.2.c) Cytostatic and cytotoxic proteins

However, an antitumoral or antiinflammatory substance is also to be understood as being a DNA sequence for a protein which exhibits, directly or indirectly, a cytostatic effect on tumors. These proteins include, in particular:
  antibodies or antibody fragments
  perforin
  granzyme
  IL-2
  IL-4
  IL-12
  interferons, for example
    IFNα
    IFNβ
    IFNγ
  TNF
    TNFα
    TNFβ
  oncostatin M
  sphingomyelinase (Jarvis et al. *PNAS-USA* 91, 73, (1994)) and
  magainin and magainin derivatives (Cruciani et al., *PNAS* 88, 3792 (1991); Jacob et al., *Ciba Found. Symp.* 186, 197 (1994); Peck-Miller et al., *Cancer Chemoth. Pharmac.* 32, 109 (1993)).

2.2.d) Inflammation inducers

An antitumoral substance further may be the DNA sequence encoding a protein which, where appropriate in addition to having an antitumoral effect, stimulates inflammation and thereby contributes to the elimination of tumor cells. Examples of these proteins are, in particular:
  RANTES (MCP-2)
  monocyte chemotactic and activating factor (MCAF)
  IL-8
  macrophage inflammatory protein 1 (MIP-1α, -β)
  neutrophil activating protein 2 (NAP-2)

IL-3
IL-5
human leukemia inhibitory factor (LIF)
IL-7
IL-11
IL-13
GM-CSF
G-CSF
M-CSF cobra venom factor (CVF) or constituent sequences of CVF which correspond functionally to human complement factor C3b, i.e., which can bind to complement factor B and, after cleavage by factor D, constitute a C3 convertase. The DNA sequences for CVF and its constituent sequences were published by Fritzinger et al., Proc. Natl. Acad. Sci. USA 91, 12775 (1994).

human complement factor C3 or its constituent sequence C3b. The DNA sequence for C3 and its constituent sequences was published by De Bruijn et al., Proc. Natl. Acad. Sci. USA 82, 708 (1985).

cleavage products of human complement factor C3 which resemble CVF functionally and structurally. Cleavage products of this nature were described by O'Keefe et al., J. Biol. Chem. 263, 12690 (1988).

bacterial proteins which activate complement or induce inflammations, such as porins of Salmonella typhimurium (Galdiero et al., Infection and Immunity 46, 559 (1984)), clumping factors of Staphylococcus aureus (EspersenActa. Path. Microb. et Imm. Scandin. Sect. C 93, 59 (1985)), modulins, particularly of Gram-negative bacteria (Henderson et al., Inflam. Res. 44, 187 (1995)), major outer membrane proteins of legionellas (Bellinger-Kawahara et al., J. Exp. Med. 172, 1201 (1990)) or of Haemophilus influenzae type B (Hetherington et al., Infection and Immunity 60, 19 (1992)) or of klebsiellas (Alberti et al., Infection and Immunity 61, 852 (1993)) or M molecules of group G streptococci (Campo et al., J. Infec. Dis. 171, 601 (1995)).

DNA sequences of fusion proteins formed between the listed cytokines or growth factors, on the one hand, and ligands for receptors on the cell membrane (for example an antibody which is specific for endothelial cells or tumor cells, or the Fc moiety of human immunoglobulin), on the other hand, can also be used as an active substance within the invention. DNA sequences encoding such proteins include those described, for example, in EP-A 0 464 633 A1.

2.2.e) Enzymes for activating precursors of cytostatic agents

However, an antitumoral or antiinflammatory substance is also to be understood to include a DNA sequence encoding an enzyme which is able to convert precursors of an antitumoral active compound into an antitumoral active compound. Such enzymes, which cleave inactive precursor substances (prodrugs), thereby forming active cytostatic agents (drugs), and the relevant prodrugs and drugs in each case, have already been reviewed by Deonarain et al. (Br. J. Cancer 70, 786 (1994)), by Mullen, (Pharmac. Ther. 63, 199 (1994)) and by Harris et al. (Gene Ther. 1, 170 (1994)).

For example, the DNA sequences of one of the following enzymes may be used:

herpes simplex virus thymidine kinase (Garapin et al., PNAS USA 76, 3755 (1979), Vile et al., Cancer Res. 53, 3860 (1993), Wagner et al., PNAS USA 78, 1441 (1981), Moelten et al., Cancer Res. 46, 5276 (1986), J. Natl. Cancer Inst. 82, 297 (1990))

varicella zoster virus thymidine kinase (Huber et al., PNAS USA 88, 8039 (1991), Snoeck, Int. J. Antimicrob. Agents 4, 211 (1994))

bacterial nitroreductase (Michael et al., FEMS Microbiol. Letters 125, 195 (1994), Bryant et al., J. Biol. Chem. 266, 4126 (1991), Watanabe et al., Nucleic Acids Res. 18, 1059 (1990))

bacterial β-glucuronidase (Jefferson et al., PNAS USA 83, 8447 (1986))

plant β-glucuronidase from Secale cereale (Schulz et al., Phytochemistry 26, 933 (1987))

human β-glucuronidase (Bosslet et al., Br. J. Cancer 65, 234 (1992), Oshima et al., PNAS USA 84, 685 (1987))

human carboxypeptidase (CB) e.g.
  mast cell CB-A (Reynolds et al., J. Clin. Invest. 89, 273 (1992))
  pancreatic CB-B (Yamamoto et al., J. Biol. Chem. 267, 2575 (1992), Catasus et al., J. Biol. Chem. 270, 6651 (1995))
  bacterial carboxypeptidase (Hamilton et al., J. Bacteriol. 174, 1626 (1992), Osterman et al., J. Protein Chem. 11, 561 (1992))

bacterial β-lactamase (Rodrigues et al., Cancer Res. 55, 63 (1995), Hussain et al., J. Bacteriol. 164, 223 (1985), Coque et al., EMBO J. 12, 631 (1993))

bacterial cytosine deaminase (Mullen et al., PNAS USA 89, 33 (1992), Austin et al., Mol. Pharmac. 43, 380 (1993), Danielson et al., Mol. Microbiol. 6, 1335 (1992))

human catalase or peroxidase (Ezurum et al., Nucl. Acids Res. 21, 1607 (1993))

phosphatase, in particular
  human alkaline phosphatase (Gum et al., Cancer Res. 50, 1085 (1990))
  human acid prostate phosphatase (Sharieff et al., Am. J. Hum. Gen. 49, 412 (1991), Song et al., Gene 129, 291 (1993), Tailor et al., Nucl. Acids Res. 18, 4928 (1990))
  type 5 acid phosphatase (Gene 130, 201 (1993))

oxidase, in particular
  human lysyloxidase (Kimi et al., J. Biol. Chem. 270, 7176 (1995))
  human acid D-aminooxidase (Fukui et al., J. Biol. Chem. 267, 18631 (1992))

peroxidase, in particular
  human glutathione peroxidase (Chada et al., Genomics 6, 268 (1990), Ishida et al., Nucl. Acids Res. 15, 10051 (1987))
  human eosinophil peroxidase (Ten et al., J. Exp. Med. 169, 1757 (1989), Sahamaki et al., J. Biol. Chem. 264, 16828 (1989))
  human thyroid peroxidase (Kimura, PNAS USA 84, 5555 (1987)).

galactosidases

In order to facilitate secretion of the listed enzymes, the homologous signal sequence which is in each case contained in the DNA sequence can be replaced by a heterologous signal sequence which improves extracellular secretion. Thus, for example, the signal sequence of β-glucuronidase (DNA position ≦27 to 93; Oshima et al., PNAS 84, 685 (1987)) can be replaced with the signal sequence for immunoglobulin (DNA position ≦63 to ≧107; Riechmann et al., Nature 332, 323 (1988)) or with the signal sequence for CEA (DNA position ≦33 to ≧134; Schrewe et al., Mol. Cell. Biol. 10, 2738 (1990), Berling et al., Cancer Res. 50, 6534 (1990))

or with the signal sequence of human respiratory syncytial virus glycoprotein (cDNA of amino acids ≦38 to ≧50 or 48 to 65; Lichtenstein et al., *J. General Virol.* 77, 109 (1996)).

In addition, preference is to be given to selecting DNAs of those enzymes which, as the result of point mutation, are stored to a lesser extent in lysosomes and secreted to a greater extent. Point mutations of this nature have been described for β-glucuronidase, for example (Shiplex et al., *J. Biol. Chem.* 268, 12193 (1993)).

A sequence for a transmembrane domain can be inserted, as an alternative to, or in addition to, the signal sequence, for the purpose of anchoring the enzyme into the cell membrane of the enzyme-forming cell. Thus, for example, the transmembrane sequence of human macrophage colony-stimulating factor (DNA position ≦1485 to ≧1554; Cosman et al., *Behring Inst. Mitt.* 83, 15 (1988)) or the DNA sequence for the signal region and transmembrane region of human respiratory syncytial virus (RSV) glycoprotein G (amino acids 1 to 63 or their constituent sequences, amino acids 38 to 63; Vijaya et al., *Mol. Cell Biol.* 8, 1709 (1988), Lichtenstein et al., *J. General Virol.* 77, 109 (1996)) or the DNA sequence for the signal and transmembrane regions of influenza virus neuraminidase (amino acids 7 to 35 or the constituent sequence amino acids 7 to 27; Brown et al., *J. Virol.* 62, 3824 (1988)) can be inserted between the DNA sequence for the promoter and the DNA sequence for the enzyme (e.g., the β-glucuronidase).

The nucleotide sequence

GCCACC or

GCCGCC can be inserted (Kozak, *J. Cell. Biol.* 108, 299 (1989) at the 3' end of the promoter, and directly prior to the 5' end of the start signal (ATG) of the signal or transmembrane sequence, for the purpose of augmenting translation.

However, the nucleotide sequence for a glycophospholipid anchor can also be inserted for the purpose of anchoring the enzyme in the cell membrane of the enzyme-forming cells. A glycophospholipid anchor is inserted at the 3' end of the nucleotide sequence for the enzyme, and this insertion can be in addition to the insertion of a signal sequence. Glycophospholipid anchors have been described, for example, for CEA (DNA position ≦893 to ≧1079; Berling et al., *Cancer Res.* 50, 6534 (1990)), and for N-CAM (Cunningham et al., *Science* 236, 799 (1987), and for other membrane proteins, such as Thy-1 (Clissold, *Biochem. J.* 281, 129 (1992)) or CD16 (Selvaray et al., *Nature* 333, 565 (1988)). Ferguson et al. (*Ann. Rev. Biochem.* 57, 285 (1988)) have published a review of glycophospholipid-anchored membrane proteins.

Another option for anchoring enzymes to the cell membrane in accordance with the present invention is to use a DNA sequence for a ligand-enzyme fusion protein. The specificity of the ligand of this fusion protein is directed against a membrane structure which is present on the cell membrane of proliferating endothelial cells or of tumor cells.

Ligands which bind to the surface of proliferating endothelial cells include; for example, antibodies or antibody fragments which are directed against membrane structures of endothelial cells, as described, for example, by Burrows et al. (*Pharmac. Ther.* 64, 155 (1994)), Hughes et al. (*Cancer Res.* 49, 6214 (1989)) and Maruyama et al. (*PNAS USA* 87, 5744 (1990)). These antibodies include, in particular, antibodies against the VEGF receptors.

The murine monoclonal antibodies are preferably to be employed in humanized form. The humanization is effected in the manner described by Winter et al. (*Nature* 349, 293 (1991)) and Hoogenbooms et al. (*Rev. Tr. Transfus. Hemobiol.* 36, 19 (1993)). Antibody fragments are prepared in accordance with the state of the art, for example in the manner described by Winter et al. (*Nature* 349, 293 (1991)), Hoogenboom et al. (*Ref. Tr. Transfus. Hemobiol.* 36, 19 (1993); Girol. Mol. Immunol. 28, 1379 (1991) or Huston et al. (*Intern. Rev. Immunol.* 10, 195 (1993)).

The ligands furthermore include all active compounds which bind to membrane structures or membrane receptors on endothelial cells. For example, they include substances which contain mannose terminally, and, in addition, IL-1 or growth factors, or their fragments or constituent sequences thereof, which bind to receptors which are expressed by endothelial cells, such as PDGF, bFGF, VEGF, and TGFB (Pusztain et al., *J. Pathol.* 169, 191 (1993)). In addition, they include adhesion molecules which bind to activated and/or proliferating endothelial cells. Adhesion molecules of this nature, such as SLex, LFA-1, MAC-1, LECAM-1 or VLA-4, have already been described (reviews in Augustin-Voss et al., *J. Cell. Biol.* 119, 483 (1992), Pauli et al., *Cancer Metast. Rev.* 9, 175 (1990) and Honn et al., *Cancer Metast. Rev.* 11, 353 (1992)).

The ligands also include antibodies, or their fragments, which are directed against tumor-specific or tumor-associated antigens on the tumor cell membrane. Examples of such antigens and the affiliated antibodies are described in Sedlacek et al., *Contrib. Oncol.* 32 (1988) and *Contrib. Oncol.* 43 (1992). Antibody-enzyme fusion proteins were described, for example, by Bosslet et al., *Br. J. Cancer* 65, 234 (1992). In order to facilitate secretion of the listed ligand-enzyme fusion proteins, the homologous signal sequence which is in each case contained in the DNA sequence of the enzyme can, as already described, be replaced with a heterologous signal sequence which improves extracellular secretion.

2.2.f) Ribozymes

The antitumoral or antiinflammatory substance of the invention can also be a DNA sequence encoding a ribozyme which is able to cleave, and thereby inactivate, the transcription product (messenger RNA) of a gene for a cell-cycle control protein. Preferred substrates for ribozymes of this nature are the messenger RNAs of the genes of cyclin A, cyclin B, cyclin D1, cyclin E, cdc2, cdc25C and DP1. The DNA oligonucleotide sequence for a ribozyme which cleaves cyclin D1 mRNA (Xiong et al., *Cell* 665, 691 (1991) in the nucleotide position
is, for example,
SEQ ID NO.: 1
5'-AGCTTCCGCATGCTGATGAGGCCGCAAGG CCGAAACGGCAG-3'
or
SEQ ID NO.: 2
5'-AATTCTGCCGTTTCGGCCTTGCGGCCTCAT CAGCATGCGGA-3'

The DNA oligonucleotide sequence for another ribozyme for cleaving the cyclin D1 mRNA in the nucleotide position is, for example,
SEQ ID NO.: 3
5'-AGCTTCCAGCCTGATGAGGCCGCAAGGCC GAAACAGGAAG-3'
or
SEQ ID NO.: 4
5'-AATTCTTCCTGTTTCGGCCTTGCGGCCTCA TCAGGCTGGA-3'

The DNA oligonucleotide sequence for a ribozyme which cleaves the MRNA of cyclin E (Koff et al., *Cell* 66, 1217 (1991)) in the nucleotide position
is, for example, SEQ ID NO.: 5
5'-AGCTTGCACACTGATGAGGCCGCA
AGGCCGAAACTGCG-3'
SEQ ID NO.: 6
5'-AATTCGCAGTTTCGGCCTTGCGGC
CTCATCAGTGTGCA-3'

The DNA oligonucleotide sequence for another ribozyme for cleaving the mRNA of cyclin E in the nucleotide position is, for example,
SEQ ID NO.: 7
5'-AGCTTGAAGTTTATACTGATGAGG
CCGCAAGGCCGAAACTTCAG-3'
or
SEQ ID NO.: 8
5'-AATTCTGAAGTTTCGGCCTTGCGG
CCTCATCAGTATAAACTTCA-3'

2.3. Combination of several antitumoral or antiinflammatory substances

Figure 11:
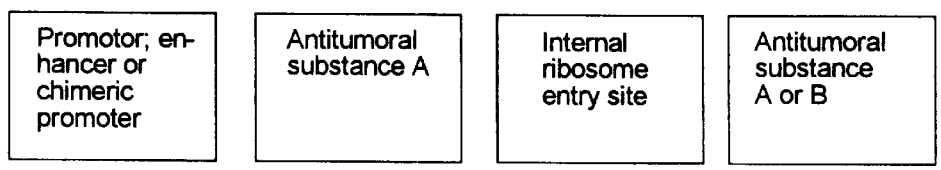
FIG. 11 is a diagram of the components of another nucleic acid construct of the present invention.

The invention furthermore relates to nucleic acid constructs in which there is a combination of the DNA sequences of several identical antitumoral or antiinflammatory substances (A,A) or of different antitumoral substances (A,B). In order to express two DNA sequences, the cDNA of an internal ribosome entry site (IRES) is preferably interposed as a regulatory element. This is illustrated by FIG. 11.

IRES sequences of this embodiment are described, for example, by Mountford and Smith (*TIG* 11, 179 (1995), Kaufman et al., *Nucl. Acids Res.* 19, 4485 (1991), Morgan et al., *Nucl. Acids Res.* 20, 1293 (1992), Dirks et al., *Gene* 128, 247 (1993), Pelletier and Sonenberg, *Nature* 334, 320 (1988) and Sugitomo et al., *BioTechn.* 12, 694 (1994). Thus, the cDNA of the IRES sequence of polio virus (position 140 to 630 of the 5' UTR; Pelletier and Sonenberg, *Nature* 334, 320 (1988)) can be used to link the DNA of the antiinflammatory substance A (at the 3' end) and the DNA of the antiinflammatory substance B (at the 5' terminus).

Depending on the combination, an active compound of this embodiment exhibits an additive (A+A, A+B1) or synergistic effect.

3. Active compound for remedying deficient formation of blood cells 3.1. Selection of the promoters or the activator sequences for hematopoietic cells A promoter or activator sequence composed of promoters or enhancers is preferably used which is a gene-regulatory sequence or an element from a gene which encodes a protein which is particularly strongly or selectively expressed in hematopoietic cells. Such gene-regulatory sequences include promoter sequences for genes of a cytokine or its receptor, whose expression in the immature hematopoietic cells (or in neighboring cells such as the stroma) precedes the subsequent cytokine, which exerts an effect on the hematopoietic cells and which is desired in an active substance. Examples of such cytokines which exert an effect on immature hematopoietic cells are:

stem cell factor
IL-1
IL-3
IL-6
GM-CSF 3.2. Selection of the structural gene for active substances for hematopoietic cells An active substance of the invention can also be a DNA sequence whose expressed protein brings about proliferation and/or differentiation of blood cells.

4. Active compound for the therapy of autoimmune diseases, allergies and inflammations and for preventing organ rejections 4.1. Selection of the promoters or the activator sequences for inter alia autoimmune diseases Gene-regulatory sequences of the genes encoding those proteins which are formed to an increased extent in macrophages and/or in lymphocytes during an immune reaction can be used as promoters or activator sequences composed of promoters or enhancers. Examples of such proteins are:

IL-1
IL-1β
IL-1 receptor
IL-2
IL-2 receptor
IL-3
IL-3 receptor
IFN-γ
IL-4
IL-4 receptor
IL-5
IL-6
LIF
IL-7
IL-10
IL-11
IL-12
IL-13
GM-CSF
GM-CSF receptor
integrin beta 2 proteins 4.2. Selection of the genes for active substances to treat, e.g., autoimmune diseases The active substance of the invention can also be a DNA sequence encoding a cytokine, a chemokine, a growth factor, or one of their inhibitors, a ribozyme which is catalytic for the transcription product of one of these DNA sequences or the transcription product of a gene which encodes a cell-cycle control protein or a DNA sequence for an antibody or an antibody fragment or for an enzyme or for a fusion protein of an antibody, cytokine or growth factor with an enzyme. The selection of the active substance depends on the underlying disease to be treated and on the promoter sequence which is selected.

5. Active compound for treating arthritis 5.1. Selection of the promoters or the activator sequences for arthritis Promoters or activator sequences composed of promoters or enhancers are preferably used which are gene-regulatory sequences of those genes with which transcription factors interact which are formed or are active in endothelial cells, synovial cells and inflammatory cells. The preferred promoter sequences include gene-regulatory sequences or elements from genes which encode proteins which are characteristically expressed in endothelial cells, synovial cells and inflammatory cells.

5.2. Selection of the structural genes for active substances for arthritis

An active substance of the invention is also a DNA sequence whose expressed protein directly or indirectly inhibits inflammation, for example in a joint, and/or promotes the reconstitution of extracellular matrix (cartilage and connective tissue) in the joint.

6. Preparation of an active compound against infectious agents

The active compound can be prepared in two fundamentally different forms:

for the therapy of virus infections and parasite invasions, or else for the prophylaxis of infectious diseases caused by viruses, bacteria or parasites.

Vaccines are used for the prophylaxis of infectious diseases. However, the possibilities of preparing effective vaccines in a conventional manner are limited (Brown, *Int. J. Technol. Assessm. Health Care* 10, 161 (1994)), Ellis, *Adv. Exp. Med. Biol.* 327, 263 (1992)) and Arnon et al., *FASEB J.* 6, 3265 (1992)). As a result, the technology of DNA vaccines has been developed. These DNA vaccines have been characterized with regard to degree of efficacy, safety and side effects (Fynan et al., *Int. J. Immunopharm.* 17, 79 (1995), Donnelly et al., *Immunol.* 2, 20 (1994)).

Active compounds for the prophylaxis of infectious diseases of the invention are selected having a high degree of safety due to their cell specificity and cell cycle regulation.

6.1. Selection of the promoters or activator sequences 6.1.a) For the therapy of infectious diseases Promoter sequences of cell genes whose activity is specifically altered by infections with bacterial parasites, or promoter sequences of those viruses which transform the cells they infect and stimulate them to proliferate, are preferred as activator sequences. These viruses include, for example, HBV, HCV, HSV, HPV, HIV, EBV and HTLV.

6.2. Selection of the structural genes for active substances 6.2.a) For the therapy of infectious diseases The DNA of a protein which exhibits cytostatic, cytotoxic or antiviral effects may also be selected as the active substance. Examples of cytotoxic or cytostatic proteins have already been listed above. When an enzyme is selected, the precursor which can be cleaved by this enzyme, and which is the precursor of an antiviral, cytotoxic or antiparasitic substance, has to be administered subsequently. Antivirally active cytokines and growth factors are also active substances for antiviral proteins within the invention. They include, for example, the DNA sequences encoding the following active substances:

IFNα
IFNβ
IFNγ
TNFβ
TNFα
IL-1
TGFβ.

However, DNA sequences for protein fusions between the listed cytokines, growth factors, or the extracellular moiety of the receptors, on the one hand, and a ligand, on the other hand, can also be used as active substances of the invention; for example, fusion proteins containing the Fc moiety of human immunoglobulin have been described in EP-A 0 464 633 A1.

Genes for ribozymes which digest the mRNA of genes for cell-cycle control proteins or the mRNA of viruses are also utilized as active substances. Ribozymes which are catalytic for HIV were reviewed, for example, by Christoffersen et al., *J. Med. Chem.* 38, 2033 (1995).

A suitable active substance is also the DNA sequence encoding an antibody which inactivates the particular virus, or its VH-containing and VL-containing fragments, or its VH and VL fragments which are connected by way of a linker, and which is/are prepared, for example, in accordance with the methodology described by Marasco et al. (*Proc. Natl. Acad. Sci. USA* 90, 7889 (1993)) Examples of antibodies having such a specificity against viruses are listed in Section 8.4.

6.2.b) For the prophylaxis of infectious diseases

The DNA of a protein which is formed by the infectious agent and which leads, by means of triggering an immune reaction, i.e., by means of antibody binding and/or by means of the action of cytotoxic T lymphocytes, to the neutralization and/or destruction of the pathogen may also be the active substance. So-called neutralization antigens are already being employed as vaccine antigens (see review in Ellis, *Adv. Exp. Med. Biol.* 327, 263 (1992)). Examples of DNA sequences which encode neutralization antigens can be obtained from the following publications:

influenza A-virus antigen
(Ulmer et al., *Science* 259, 1745 (1993), Robinson et al., *Vaccine* 11, 957 (1993), Fynan et al., *Int. J. Immunopharmac.* 17, 79 (1995))

HIV antigens
(Wang et al., *PNAS USA* 90, 4156 (1993))

rabies virus antigen
(Donnelly et al., *Immunol.* 2/1, 20 (1994))

HSV (herpes simplex virus) antigen
(Fleckenstein et al., *Nature* 274, 57 (1978))

RSV (respiratory syncytial virus) antigen
(Du et al., *Bio/Tech.* 12, 813 (1994), Hall, *Science* 265, 1393 (1993))

parainfluenza virus antigen
(Du et al., *Bio/Techn.* 12, 813 (1994))

rotavirus antigen
(Albert et al., *J. Clin. Microbiol.* 25, 183 (1987), Anderson et al., *J. Infect. Dis.* 153, 823 (1986), Battaglia et al., *J. Infect. Dis.* 155, 140 (1987), Chanock et al., *J. Infect. Dis.* 148, 49 (1983), Dyall-Smith et al., *J. Virol.* 38, 1099 (1981), Glass et al., *Science* 265, 1389 (1994))

VZV (varicella zoster virus) antigen
(Straus et al., *Ann. Intern. Med.* 109, 438 (1988), Gershon, *Pediatr. Infect. Dis.* 2, 171 (1991), Kinchington et al., *J. Virol.* 64, 4540 (1990))

CMV (cytomegalovirus) antigen
(Plotkin, *Science* 265, 1383 (1994))

measles virus antigen
(Katz and Kellin, *Science* 265, 1391 (1994))

HPV (human papilloma virus) antigen
(Tindl and Frazer, *Curr. Topics Microbiol. Immunol.* 186, 217 (1994))

HBV (hepatitis B virus) antigen
(Valenzuela et al., *Nature* 280, 815 (1979), Heerman et al., *J. Virol.* 52, 396 (1984))

HCV (hepatitis C virus) antigen
(Cerny et al., *Curr. Topics Microbiol. Immunol.* 189, 169 (1994), Esteban et al., *Progr. Liver Dis.* 10, 253 (1992), Jung et al., *Eur. J. Clin. Invest.* 24, 641 (1994))

HDV (hepatitis D virus) antigen
(Iwarson, *Scand. J. Infect. Dis.* 24, 129 (1992), Consolo et al., *Nephron.* 61, 251 (1992))

HEV (hepatitis E virus) antigen
(Iwarson, Scand. J. Infect. Dis. 24, 129 (1992), Consolo et al., *Nephron.* 61, 251 (1992))

HAV (hepatitis A virus) antigen
(d'Hondt, *Vaccine* 10, 48 (1992), Andre, *J. Infect. Dis.* 171, 33 (1995), Lemon et al., *Vaccine* 10, 40 (1992), Melnick et al., *Vaccine* 10, 24 (1992), Flehmig, *Baillieres Clin. Gastroenterol.* 4, 707 (1990))

*Vibrio cholerae* antigen
(Levine and Kaper, *Vaccine* 11, 207 (1993))

*Borrelia burgdorferi* antigen
(Schaible et al., *Immunol. Letters* 36, 219 (1993), Wallich et al., *Lab. Med.* 17, 669 (1993))

Helicobacter pylori antigen
(Crabtree et al., *Lancet* 338, 332 (1991), Blaser, *J. Infect. Dis.* 161, 626 (1990), Cover and Blaser, *J. Biol. Chem.* 267, 10570 (1993), Cover et al., *Infect. Immunol.* 58, 603 (1990), Dunn et al., *J. Biol. Chem.* 265, 9464 (1990), Dunn et al., *Infect. Immunol.* 60, 1946 (1992), Lage et al., *Acta Gastroenterol. Belg.* 56 (suppl.), 61 (1993), Mobley et al., *Scand. J. Gastroint.* 26 (suppl. 187), 39 (1991))

malaria antigen
(Nussenzweig and Long, *Science* 265, 1381 (1994), Maurice, *Science* 267, 320 (1995), Enders et al., *Vaccines* 10, 920 (1992), Knapp et al., *Infect. Imm.* 60, 2397 (1992)).

However, active substances of the invention also include the DNA of an antiidiotype antibody or its antigen-binding fragments, whose antigen-binding structures, the complementarity-determining regions, constitute copies of the protein or carbohydrate structure of the neutralization antigen of the infectious agent. Such antiidiotype antibodies can, in particular, replace carbohydrate antigens in the case of bacterial infectious agents. Such antiidiotypic antibodies and their cleavage products are reviewed by Hawkins et al (*J. Immunotherapy* 14, 273 (1993)) and Westerink and Apicella (*Springer Seminars in Immunopathol.* 15, 227 (1993)).

Figure 12:
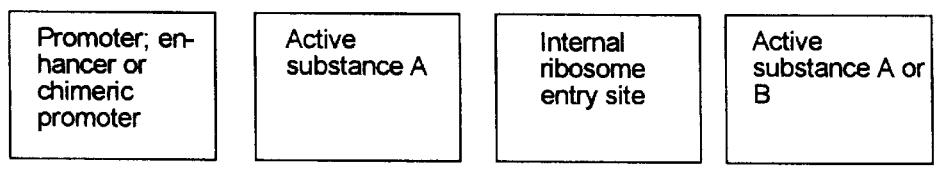
FIG. 12 is a diagram of the components of another nucleic acid construct of the present invention.

6.3. Combination of identical or different active substances for the therapy or prophylaxis of infectious diseases The invention additionally relates to an active compound in which there is a combination of the DNA sequences of identical active substances (A,A) or different active substances (A,B). For the expression of two sequences, the cDNA of an internal ribosome entry site (IRES) is preferably interposed as a regulatory element. Such IRES sequences are described, for example, by Montford and Smith (*TIG* 11, 179 (1995), Kaufman et al., *Nucl. Acids Res.* 19, 4485 (1991), Morgan et al., *Nucl. Acids Res.* 20, 1293 (1992), Dirks et al., *Gene* 128, 247 (1993), Pelletier and Sonnenberg, *Nature* 334, 320 (1988) and Sugitomo et al., *BioTechn.* 12, 694 (1994). Thus, the cDNA of the IRES sequence of polio virus (position 140 to 630 of the 5' UTR (Pelletier and Sonenberg, *Nature* 334, 320 (1988)) can be used to link the DNA of the antiviral substance A (at the 3' end) and the DNA of the antiviral substance B (at the 5' terminus). This is illustrated by FIG. 12.

Depending on the combination, an active compound of this embodiment exhibits an additive (A+A, A+B1) or synergistic effect.

Two identical or two different antiviral active substances can be combined with each other for the therapy of virus diseases, for example.

In the prophylaxis of infectious diseases, several active substances, which encode different antigens of an infectious agent or of different infectious agents, can be combined with each other. Furthermore, the active substance which encodes the antigen of an infectious agent can be combined with an active substance which encodes a cytokine or a cytokine receptor. The cytokines or cytokine receptors which are thereby formed (after injection of the active compound) at the same time as the infectious agent antigen can influence the nature and strength of the immune reaction which develops. DNA sequences for cytokines and cytokine receptors which amplify the humoral immune reaction have already been described in 6.2.d), while those for cytokines and cytokine receptors which amplify the cellular immune reaction have been described in 6.2.a) and 6.2.c).

Examples of DNA sequences for cytokines which amplify the immune reaction as a whole are:

IL-1α
(Fenton, *Int. J. Immunopharm.* 14, 401 (1992), Furntani et al., *Nucl. Acids Res.* 14, 3167 (1986), Lafage et al., *Blood* 73, 104 (1989), March et al., *Nature* 315, 641 (1985))

IL-1β
(Bensi et al., *Gene* 52, 95 (1987), Auron et al., *PNAS* 81, 7907 (1984), Clark et al., *Nucl. Acids Res.* 14, 7897 (1986))

IL-2
(Fletscher et al., *Lymphok. Res.* 6, 45 (1987), Matsui et al., *Lymphokines* 12, 1 (1985), Tanaguchi et al., *Nature* 302, 305 (1983))

GM-CSF
(Gough et al., *Nature* 309, 763 (1984), Nicola et al., *J. Biol. Chem.* 254, 5290 (1979), Wong et al., *Science* 228, 810 (1985))

7. Active compound for treating leukemias and tumors 7.1. Selection of the promoters or activator sequences for leukemias A gene-regulatory nucleotide sequence with which transcription factors interact which are formed or active in leukemia cells or tumor cells may be used as the promoter or activator sequence. Preferred promoters or activator sequences include gene-regulatory sequences or elements from genes which encode proteins which are formed particularly in leukemia cells or tumor cells.

7.2. Selection of the structural genes for active substances for leukemias

An active substance of the invention can be a DNA sequence whose expressed protein directly or indirectly inhibits the proliferation of cells, in particular also of leukemia cells or tumor cells. These active substances include, for example, the DNA sequences for inhibitory, cytostatic, apoptosis-inducing or cytotoxic proteins, or of enzymes, as have already been described.

An active substance furthermore can be the DNA sequence encoding a ribozyme which catalyzes cleavage of the mRNA of the genes for cell-cycle control proteins.

8. Active compound for inhibiting the proliferation of smooth muscle cells in vascular occlusions 8.1. Selection of the promoters or the activator sequences for smooth muscle cells Gene-regulatory sequences or elements from genes which encode proteins which are formed in particular in smooth muscle cells are preferably to be used as promoters or activator sequences composed of promoters or enhancers.

8.2. Selection of structural genes for active substances for smooth muscle cells An active substance of the invention is also a DNA sequence whose expressed protein inhibits the proliferation of smooth muscle cells. These inhibitors of proliferation include the proteins which have already been mentioned in 2.2.a) and 2.2.c). However, an active substance can also be the DNA sequence for an enzyme which converts an inactive precursor of a cytostatic agent into a cytostatic agent (see 2.2.e)). In addition, an active substance can also be the DNA sequence encoding a ribozyme which is specific for the mRNA of genes for cell-cycle control proteins (see 2.2.f)).

9. Active compound for inhibiting or promoting coagulation 9.1. Selection of the promoters or the activator sequences for inhibiting coagulation Gene-regulatory sequences or elements from genes which encode proteins which can be detected in smooth muscle cells, in activated endothelial cells, in activated macrophages or in activated lymphocytes are preferably used as promoters or activator sequences of the invention.

9.1.a) Smooth muscle cells

Examples of promoter sequences for genes in smooth muscle cells have already been mentioned.

9.1.b) Activated endothelial cells

Examples of proteins which are formed in particular in activated endothelial cells have been described by Burrows et al. (*Pharmac. Ther.* 64, 155 (1994)). In particular, these proteins which occur to an increased extent in endothelial cells include, for example, those proteins which have already been listed above, as have the promoter sequences of their genes.

9.1.c) Activated macrophages and/or activated lymphocytes

Activator sequences can also be the promoter sequences of the genes for proteins which are formed to an increased extent in macrophages and/or lymphocytes during the immune reaction. Proteins of this nature have already been listed.

9.2. Selection of the structural genes for active substances for inhibiting or promoting coagulation A DNA sequence which encodes a protein which directly or indirectly inhibits thrombocyte aggregation or a blood coagulation factor, or stimulates fibrinolysis, can be used as an active substance for inhibiting coagulation. Such an active substance is designated as a coagulation inhibitor. Genes encoding, for example, plasminogen activators (PA), for example tissue PA (PA) or the urokinase-like PA (uPA) or protein C, antithrombin III, C-IS inhibitor, $\mu$1 antitrypsin, tissue factor pathway inhibitor (TFPI) or hirudin, are suitable as coagulation inhibitors.

A DNA sequence which encodes a protein which directly or indirectly promotes blood coagulation is also suitable as an active substance for promoting coagulation. These proteins include, for example, blood coagulation factor VIII, blood coagulation factor IX or blood coagulation factor XIII.

10. Active compound for protecting against CNS damage 10.1. Promoters or activator sequences composed of promoters or enhancers for an active compound for protecting against CNS damage 10.1.a) Promoters or activator sequences which are activated in endothelial cells These include, in particular, the promoter sequences for the genes of endothelial-cell-specific proteins.

10.1.b) Promoters or activator sequences which are activated in glia cells

A preferred activator sequence is a nucleotide sequence (promoter sequence or enhancer sequence) which interacts with transcription factors which are formed to a particular extent, or are active, in glia cells.

10.2.) Selection of the structural genes for neurospecific factors

A neurospecific factor gene can be a DNA sequence which encodes a neuronal growth factor.

The present invention is further illustrated by, though in no way is limited to, the following examples.

EXAMPLE 1

Preparation and testing of an activator-responsive promoter unit, with the activator-responsive promoter being the sequence for binding LexA.

The novel activator-responsive promoter unit is composed of the following different nucleotide sequences, which succeed each other in the downstream direction:

Activator subunit A
  the promoter of the cdc25C gene
    (nucleic acids −290 to +121; Zwicker et al., *EMBO J.* 14, 4514 (1995); Zwicker et al., *Nucl. Acids Res.* 23, 3822 (1995))
  the cDNA for the DNA-binding domain of the LexA protein
    (amino acids 1 to 81; Kim et al., *Science* 255, 203 (1992)) or the whole LexA protein (amino acids 1 to 202; Brent et al., *Cell* 43, 729 (1985))
  the cDNA for Gal 80
    (amino acids 1 to 435; Leuther et al., *Science* 256, 1333 (1992))

Activator subunit B
  the promoter of the von Willebrand factor gene
    (nucleic acids −487 to +247; Jahroudi and Lynch, *Mol. Cell. Biol.* 14, 999 (1994))
  the cDNA for the Gal8o-binding domain of Gal4
    (amino acids 851 to 881; Leuther et al., *Science* 256, 1333 (1992))
  the SV40 nuclear localization signal (NLS)
    (SV40 large T; amino acids 126 to 132: PKKKRKV (SEQ ID NO:11); Dingwall et al., *TIBS* 16, 478 (1991))
  the HSV-1 VP16 acid transactivating domain (TAD)
    (amino acids 406 to 488; Triezenberg et al., *Genes Developm.* 2, 718 (1988); Triezenberg, *Curr. Op. Gen. Developm.* 5, 190 (1995))

Activator-responsive promoter
  the sequence for binding LexA (LexA operator) having the nucleotide sequence SEQ ID NO.:9 5'-TACTGTATGTACATACAGTA-3'(Brent et al., *Nature* 612, 312 (1984)) which is coupled to the SV40 basal promoter (nucleic acids 48 to 5191; Tooze (ed.), *DNA Tumor Viruses* (Cold Spring Harbor New York, New York; Cold Spring Harbor Laboratory).

The order of the nucleotide sequences of the activator-responsive promoter units is depicted in FIG. 13.

The activator sequence which has been described functions as follows:

The cdc25C promoter regulates transcription of the combined cDNA's for the Lex DNA-binding protein and for Gal80 in a cell cycle-specific manner.

The vWF promoter restricts transcription of the coupled cDNA for the Gal8O-binding domain of Gal4, the SV40 NSL and the TAD to endothelial cells.

The expression products of the activator subunits A and B dimerized by the Gal80-binding domain of Gal4 being bound to Gal80.

The dimerization is depicted diagrammatically in FIG. 14.

The dimeric protein constitutes a chimeric transcription factor for the LexA operator activator-responsive promoter.

Figure 15:
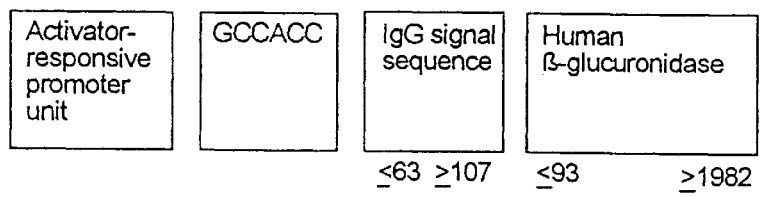
FIG. 15 is a diagram of the components of another nucleic acid construct of the present invention.

The promoter is now linked, at its 3' end, to the GCCACC sequence (Kocak, *J. Cell. Biol.* 108, 229 (1989)) and this latter is linked to the cDNA for the immunoglobulin signal peptide (nucleotide sequence ≦63 to ≧107; Riechmann et al., *Nature* 332, 323 (1988)). The cDNA for β-glucuronidase (nucleotide sequence ≦93 to ≧1982; Oshima et al., *PNAS USA* 84, 685 (1987)) is then joined to this sequence, as shown in FIG. 15. The nucleotide construct which has been prepared in this way is cloned into pUC18/19 or Bluescript-derived plasmid vectors, which are used, directly or in colloidal dispersion systems, for in-vivo administration.

The individual components of the construct are linked using suitable restriction sites, which are introduced at the termini of the different elements by way of PCR amplification. The linking is effected with the aid of enzymes which are specific for the restriction sites and which are known to the skilled person and with the aid of DNA ligases. These enzymes can be obtained commercially.

Human umbilical cord endothelial cells and fibroblasts (Wi-38) which are being maintained in culture are transfected with the described plasmid using a method known to the skilled person (Lucibello et al., *EMBO J.* 14, 132 (1995)) and the quantity of β-glucuronidase which is produced by the endothelial cells is measured using 4-methylumbelliferyl-β-glucuronide as the substrate.

In order to examine the cell-cycle specificity, endothelial cells are synchronized in G0/G1 by withdrawing methionine over a period of 48 hours (Nettelbeck et al., publication in preparation). The DNA content of the cells is determined in a fluorescence-activated cell sorter after staining with Hoechst 33258 (Lucibello et al., *EMBO J.* 14, 132 (1995)). The following results are obtained:

- No increase in β-glucuronidase can be detected in transfected fibroblasts as compared with non-transfected fibroblasts.
- Transfected endothelial cells express substantially more β-glucuronidase than do non-transfected endothelial cells.
- Proliferating endothelial cells (DNA>2 S) secrete substantially more β-glucuronidase than do endothelial cells which are synchronized in G0/G1 (DNA=2 S).

The activator-responsive promoter unit which has been described results in cell-specific, cell cycle-dependent expression of the β-glucuronidase structural gene.

Following local application, for example at the site of the tumor, or following intracranial or subarachnoid administration, or systemic, preferably intravenous or intraarterial, administration, an active compound according to the present invention has the effect of enabling, due to the cell-cycle specificity and endothelial-cell-specificity of the activator-responsive promoter unit, principally, if not exclusively, only proliferating endothelial cells to secrete β-glucuronidase. This β-glucuronidase cleaves a readily tolerated doxorubicin-β-glucuronide (Jacquesy et al., EPO 0511 917 A1), which is now injected, into doxorubicin, which has a cytostatic effect. The doxorubicin inhibits endothelial cell proliferation and has a cytostatic effect on these cells and also on adjacent tumor cells. This results in inhibition of tumor growth.

Since the active compound holds out the promise of a high degree of safety, due both to its cell specificity and its cell-cycle specificity, it can also be used for the therapy of tumor diseases at high doses and, if necessary, several times at intervals of days or weeks.

EXAMPLE 2

Preparation of a multiple promoter having a nuclear retention signal (NRS) and a nuclear export factor (NEF)

The novel multiple promoter is composed of the following different nucleotide sequences, which succeed each other in the downstream direction:

Element A
- the promoter of the cdc25C gene
  (nucleic acids –290 to +121; Zwicker et al., *EMBO J.* 14, 4514 (1995); Zwicker et al., *Nucl. Acids. Res.* 23, 3822 (1995))
- the GCCACC sequence
  (Kodak, *J. Cell. Biol.* 108, 229 (1989))
- the cDNA for the immunoglobulin signal peptide
  (nucleotide sequence ≦63 to ≧107; Riechmann et al., *Nature* 332, 323 (1988))
- the cDNA for β-glucuronidase
  (nucleotide sequence ≦93 to ≧1982; Oshima et al., *PNAS USA* 84, 685 (1987))
- the cDNA for HIV-1 virus RRE as the nuclear retention signal (NRS)
  (nucleotide sequence 7357 to 7602; Ratner et al., *Nature* 313, 277 (1985); Malim et al., *Nature* 338, 254 (1989)).

Element B
- the promoter of the von Willebrand factor (vWF) gene
  (nucleic acids –487 to +247; Jahroudi and Lynch, *Mol. Cell Biol.* 14, 999, 1994))
- the cDNA for HIV-1 virus REV as the nuclear export factor (NEF)
  (amino acid sequence 1–117; Ratner et al., *Nature* 313, 277 (1985)).

Figure 16:
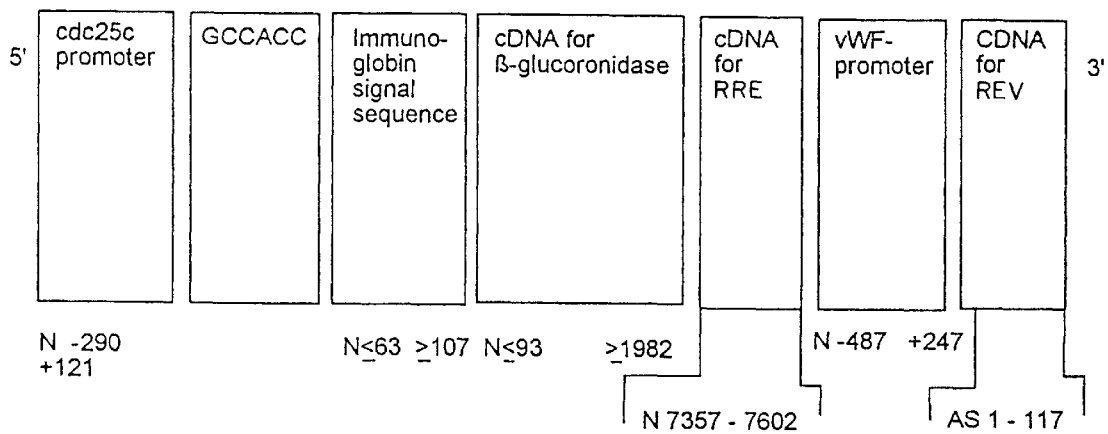
FIG. 16 is a diagram of the components of another nucleic acid construct of the present invention.

The nucleotide sequences of element A and element B are linked in accordance with the diagram in FIG. 16. The nucleotide construct which has been prepared in this way is cloned into pUC18/19 or Bluescript-derived plasmid vectors, which are used, directly or in colloidal dispersion systems, for in-vivo administration.

The individual components of the construct are linked using suitable restriction sites, which are introduced at the termini of the different elements by way of PCR amplification. The linking is effected with the aid of enzymes which are specific for the restriction sites and which are known in the art and with the aid of DNA ligases. These enzymes can be obtained commercially.

Human umbilical cord endothelial cells and fibroblasts (Wi-38) which are being maintained in culture are transfected with the described plasmid using a method known to the skilled person (Lucibello et al., *EMBO J.* 14, 132 (1995)), and the quantity of β-glucuronidase which is produced by the endothelial cells is measured using 4-methylumbelliferyl-β-glucuronide as the substrate.

In order to examine the cell-cycle specificity, endothelial cells are synchronized in G0/G1 by withdrawing methionine over a period of 48 hours (Nettelbeck et al., publication in preparation). The DNA content of the cells is determined in a fluorescence-activated cell sorter after staining with Hoechst 33258 (Lucibello et al., *EMBO J.* 14, 132 (1995)). The following results are obtained:

- No increase in β-glucuronidase can be detected in transfected fibroblasts as compared with non-transfected fibroblasts.
- Transfected endothelial cells express substantially more β-glucuronidase than do non-transfected endothelial cells.
- Proliferating endothelial cells (DNA>2 S) secrete substantially more β-glucuronidase than do endothelial cells which are synchronized in G0/G1 (DNA=2 S).

The multiple promoter unit which has been described results in cell-specific, cell cycle-dependent expression of the β-glucuronidase structural gene.

EXAMPLE 3

Preparation of an activator-responsive promoter unit in which the activator-responsive promoter is the sequence for binding Gal4.

The novel activator-responsive promoter unit is composed of the following different nucleotide sequences, which succeed each other in the downstream direction:

Activator subunit A
- the promoter of the cdc25C gene
  (nucleic acids –290 to +121; Zwicker et al., *EMBO J.* 14, 4514 (1995); Zwicker et al., *Nucl. Acids Res.* 23, 3822 (1995))
- the cDNA for the DNA-binding domain of the Gal4 protein (amino acids 1 to 147; Chasman and Kornberg, *Mol. Cell Biol.* 10, 2916 (1990))

the cDNA for Gal80
(amino acids 1 to 435; Leuther et al., *Science* 256, 1333 (1992))

Activator subunit B the promoter of the von Willebrand factor gene
(nucleic acids −487 to +247; Jahroudi and Lynck, *Mol. Cell. Biol.* 14, 999 (1994))

the cDNA for the Gal80-binding domain of Gal4
(amino acids 851 to 881; Leuther et al., *Science* 256, 1333 (1992))

the SV40 nuclear localization signal (NLS)
(SV40 large T; amino acids 126 to 132: PKKKRKV (SEQ ID NO:11); Dingwall et al., *TIBS* 16, 478 (1991))

the HSV-1 VP16 acid transactivating domain (TAD)
(amino acids 406 to 488; Triezenberg et al., *Genes Developm.* 2, 718 (1988); Triezenberg, *Curr. Opin. Gen. Developm.* 5, 190 (1995))

Activator-responsive promoter the sequence for binding Gal4, having the nucleotide sequence 5'-CGGACAACTGTTGACCG-3', SEQ ID NO: 10, (Chasman and Kornberg, *Mol. Cell Biol.* 10, 2916 (1999)), which is coupled to the SV40 basal promoter (nucleic acids 48 to 5191; Tooze (ed.), *DNA Tumor Viruses* (Cold Spring Harbor New York, New York; Cold Spring Harbor Laboratory).

Figure 17:
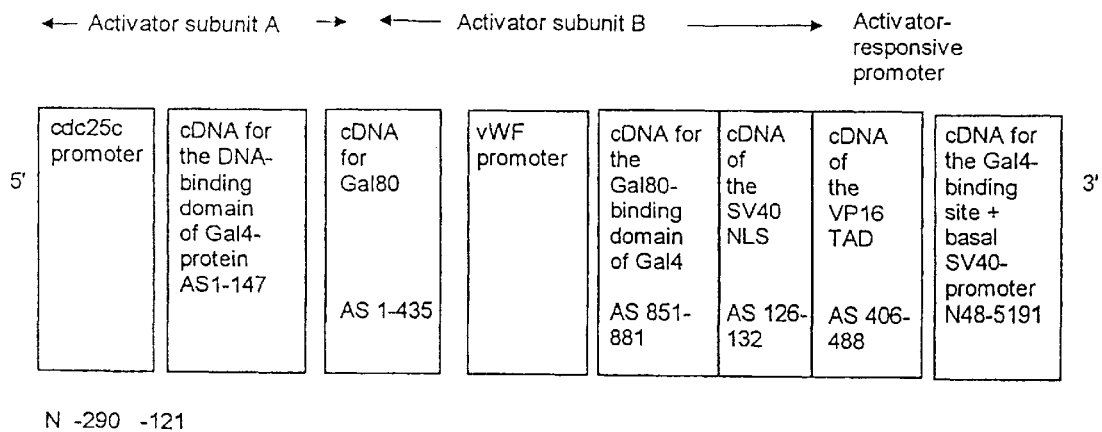
FIG. 17 is a diagram of the components of another nucleic acid construct of the present invention.

The order of the nucleotide sequences of the activator-responsive promoter units is depicted in FIG. 17.

The activator sequence which has been described functions as follows:

The cdc25C promoter regulates transcription of the combined cDNA's for the Gal4-binding protein and for Gal80 in a cell cycle-specific manner.

The promoter of the vWF gene restricts transcription of the coupled cDNA for the Gal80 -binding domain of Gal4, the SV40 NSL and the TAD to endothelial cells.

The expression products of the activator subunits A and B dimerize by the Gal80-binding domain of Gal4 being bound to Gal80.

Figure 18:
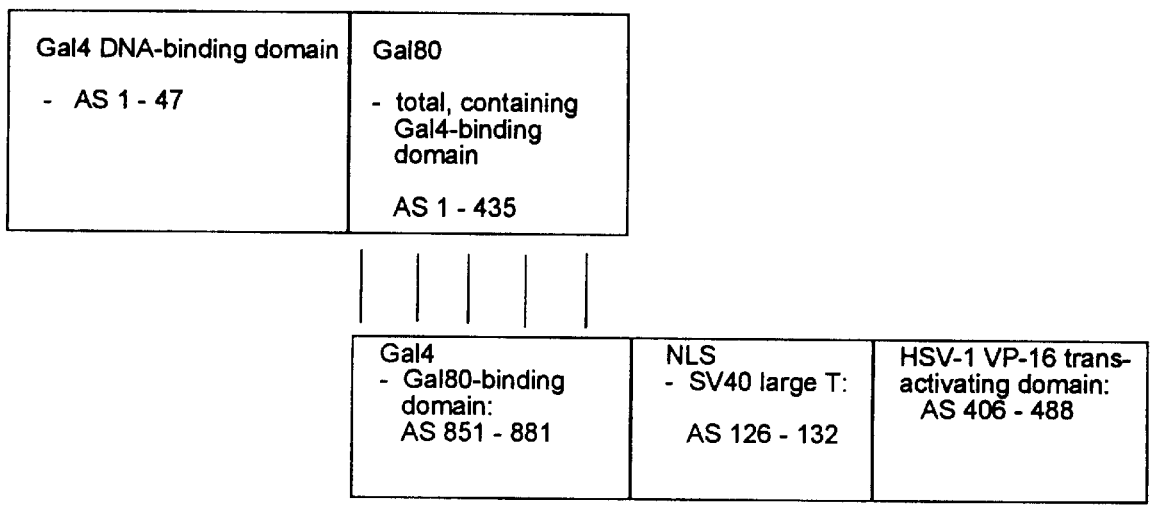
FIG. 18 is a diagram of the components of another nucleic acid construct of the present invention.

The dimerization is depicted diagrammatically in FIG. 18.

The dimeric protein constitutes a chimeric transcription factor for the activator-responsive promoter (DNA sequence for the Gal4-binding domain/SV40 promoter).

Figure 19:
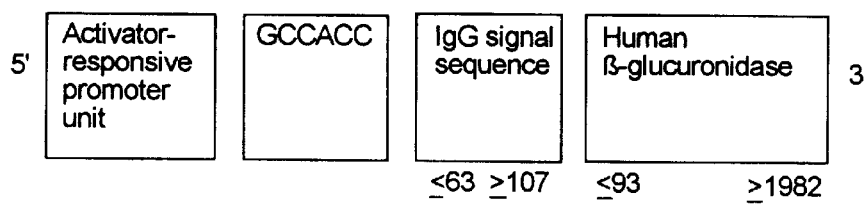
FIG. 19 is a diagram of the components of another nucleic acid construct of the present invention.

The promoter is now linked, at its 3' end, to the GCCACC sequence (Kocak, *J. Cell Biol.* 108, 229 (1989)), and this latter is linked to the cDNA for the immunoglobulin signal peptide (nucleotide sequence ≦63 to ≧107; Riechmann et al., *Nature* 332, 323 (1988)). The cDNA for β-glucuronidase (nucleotide sequence ≦93 to ≧1982; Oshima et al., *PNAS USA* 84, 685 (1987)) is joined to this sequence, as shown in FIG. 19.

The nucleotide construct which has been prepared in this way is cloned into pUC18/19 or Bluescript-derived plasmid vectors, which are used, directly or in colloidal dispersion systems, for in-vivo administration. The individual components of the construct are linked using suitable restriction sites, which are introduced at the termini of the different elements by way of PCR amplification. The linking is effected with the aid of enzymes which are specific for the restriction sites and which are known to the skilled person and with the aid of DNA ligases. These enzymes can be obtained commerically.

Human umbilical cord endothelial cells and fibroblasts (Wi-38) which are being maintained in culture are transfected with the described plasmid using a method known to the skilled person (Lucibello et al., *EMBO J.* 14, 132 (1995)), and the quantity of β-glucuronidase which is produced by the endothelial cells is measured using 4-methylumbelliferyl-β-glucuronide as the substrate.

In order to examine the cell-cycle specificity, endothelial cells are synchronized in G0/G1 by withdrawing methionine over a period of 48 hours (Nettelbeck et al., publication in preparation). The DNA content of the cells is determined in a fluorescence-activated cell sorter after staining with Hoechst 33258 (Lucibello et al., *EMBO J.* 14, 132 (1995)). The following results are obtained:

No increase in β-glucuronidase can be detected in transfected fibroblasts as compared with non-transfected fibroblasts.

Transfected endothelial cells express substantially more β-glucuronidase than do non-transfected endothelial cells.

Proliferating endothelial cells (DNA>2 S) secrete substantially more β-glucuronidase than do endothelial cells which are synchronized in G0/G1 (DNA=2 S).

The activator-responsive promoter unit which has been described results in cell-specific, cell cycle-dependent expression of the β-glucuronidase structural gene.

EXAMPLE 4

Preparation and testing of another activator-responsive promoter unit, in which the activator-responsive promoter is the sequence for binding Gal4.

This novel activator-responsive promoter unit is composed of the following different nucleotide sequences, which succeed each other in the downstream direction:

Activator subunit A the promoter of the cdc25C gene (nucleic acids −290 to +121; Zwicker et al., *EMBO J.* 14, 4514 (1995); Zwicker et al., *Nucl. Acids Res.* 23, 3822 (1995))

the SV40 nuclear localization signal (NLS) (SV40 large T, amino acids 126-132; PKKKRKV (SEQ ID NO:11), Dingwall et al., *TIBS* 16, 478 (1991))

the HSV-1 VP16 acid transactivating domain (TAD) (amino acids 406 to 488; Triezenberg et al., *Genes Developm.* 2, 718 (1988); Triezenberg, *Curr. Opin. Gen. Developm.* 5, 190 (1995))

the cDNA for the cytoplasmic moiety of the CD4 glycoprotein (amino acids 397–435; Simpson et al., *Oncogene* 4, 1141 (1989); Maddon et al., *Cell* 42, 93 (1985))

Activator subunit B the promoter of the cdc25C gene (nucleic acids −290 to +121; Zwicker et al., *EMBO J.* 14, 4514 (1995); Zwicker et al., *Nucl. Acids Res.* 23, 3822 (1995))

the SV40 nuclear localization signal (NLS) (SV40 large T; amino acids 126–132 PKKKRKV (SEQ ID NO:11); Dingwall et al., *TIBS* 16, 478 (1991))

the cDNA for the DNA-binding domain of the Gal4 protein (amino acids 1 to 147, Chasman and Kornberg, *Mol. Cell. Biol.* 10, 2916 (1990))

the cDNA for the CD4-binding sequence of the p56 lck protein (amino acids 1–71; Shaw et al., *Cell* 59, 627 (1989); Turner et al., *Cell* 60, 755 (1990); Perlmutter et al., *J. Cell. Biochem.* 38, 117 (1988))

Activator-responsive promoters

10×the binding sequence for Gal4-binding protein having the nucleotide sequence 5'-CGGACAATGTTGACCG- 3', SEQ ID NO: 10, (Chasman and Kornberg, *Mol. Cell. Biol.* 10, 2916 (1989)) the SV40 basal promoter (nucleic acids 48 to 5191; Tooze (ed). *DNA Tumor Viruses* (Cold Spring Harbor New York, N.Y., Cold Spring Harbor Laboratory)

Effector gene the cDNA for luciferase (reporter gene) (Nordeen, *Bio-Technigues* 6, 454 (1988))

The activator sequence which has been described functions as follows:

The cdc25C promoter regulates transcription of the combined cDNA's for the activating domain of VP16 and the cytoplasmic moiety of CD4 (activating subunit A) in a cell cycle-specific manner.

The cdc25C promoter additionally regulates transcription of the combined cDNA's for the DNA-binding protein of Gal4 and the CD4-binding moiety of the p56 lck protein (activating subunit B).

The expression products of activator subunits A and B dimerize by the CD4 domain being bound to the p56 lck domain.

The dimeric protein constitutes a chimeric transcription factor for the activator-responsive promoter (DNA sequence for the Gal4-binding domain/SV40 promoter) for transcription of the effector gene (=reporter gene= luciferase gene).

The nucleotide construct which has been prepared in this way is cloned into the pXP2 plasmid vector (Nordeen, *BioTechniques* 6, 454 (1988)), which is used, directly or in colloidal dispersion systems, for in-vivo administration. The individual components of the construct are linked using suitable restriction sites, which are introduced at the termini of the different elements by way of PCR amplification. The linking is effected with the aid of enzymes which are specific for the restriction sites and which are known to the skilled person and with the aid of DNA ligases. These enzymes can be obtained commercially.

3T3 fibroblasts which are being maintained in culture are transfected with the described plasmid using a method known to the skilled person (Lucibello et al., *EMBO J.* 14, 132 (1995)), and the quantity of luciferase which is produced by the fibroblasts is measured as described by Herber et al. (*Oncogene* 9, 1295 (1994)) and Lucibello et al. (*EMBO J.* 14, 132 (1995)).

In order to examine the cell-cycle specificity, the fibroblasts are synchronized in G0/G1 by withdrawing serum over a period of 48 hours. The DNA content of the cells is determined in a fluorescence-activated cell sorter after staining with Hoechst 33258 (Lucibello et al., *EMBO J.* 14, 132 (1995)).

The following results are obtained:

A marked increase in luciferase can be detected in transfected fibroblasts as compared with non-transfected fibroblasts.

Proliferating fibroblasts (DNA>2 S) form substantially more luciferase than do fibroblasts which are synchronized in G0/G1 (DNA=2 S).

The activator-responsive promoter unit which has been described results in cell cycle-dependent expression of the luciferase reporter gene.

Following local application, for example at the site of the tumor, or following intracranial or subarachnoid administration, or systemic, preferably intravenous or intraarterial, administration, an active construct according to the present invention has the effect of enabling, due to the cell-cycle specificity and endothelial-cell specificity of the activator-responsive promoter unit, principally, if not exclusively, only proliferating endothelial cells to secrete β-glucuronidase. This β-glucuronidase cleaves readily tolerated doxorubicin-β-glucuronide (Jacquesy et al., EPO 0 511 917 A1), which is now injected, into doxorubicin, which has a cytostatic effect. The doxorubicin inhibits endothelial cell proliferation and has a cytostatic effect on these cells, and also on adjacent tumor cells. This results in inhibition of the growth of the tumor.

It will be apparent to those skilled in the art that various modifications and variations can be made to the nucleic acid constructs, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 19617851.7, including its figures, claims, and abstract, for which benefit of priority under 35 USC §119 is claimed, is expressly incorporated herein in its entirety.

What is claimed is:

1. A nucleic acid construct comprising:
    (i) a nuclear retention signal selected from the group consisting of a rev-responsive element (RRE) of Human Immune Deficiency Virus-1 (HIV-1), an RRE of Human Immune Deficiency Virus-2 (HIV-2), an RRE-equivalent retention signal of a retrovirus and an RRE-equivalent retention signal of Hepatitis B virus (HBV), wherein said nuclear retention signal is operably linked to a transgene;

(ii) a first promoter sequence or enhancer sequence which activates basal transcription of the transgene;

(iii) a second promoter or enhancer sequence which activates basal transcription of a nuclear export factor, wherein at least one of said first or second promoter sequences or enhancer sequences is a chimeric promoter which interacts with an adjacent, upstream, cell-specifically, virus-specifically or metabolically activatable activator sequence which influences the expression of said transgene; and (iv) a nucleic acid which encodes a nuclear export factor selected from the group consisting of a rev gene of HIV-1, a rev gene of HIV-2, a rev gene of maedi-visna virus, a rev gene of caprine arthritis encephalitis virus, a rev gene of equine infectious anemia virus, a rev gene of feline immunodeficiency virus, a rev gene of retroviruses and a rev gene of HTLV, wherein said nuclear export factor binds to a transcription product of the nuclear retention signal and thereby mediates transport of said transcription product of the transgene out of a cell's nucleus and into the cell's cytoplasm.

2. A nucleic acid construct as claimed in claim 1 wherein a 5' end of the nuclear retention signal is linked directly or indirectly to a 3' end of the transgene.

3. A nucleic acid construct as claimed in claim 1 wherein a transcription product of the nuclear retention signal possesses a structure for binding to a nuclear export factor selected from the group consisting of a rev-gene of the viruses HIV-1, HIV-2, maedi-visna virus, caprine arthritis encephalitis virus, equine infectious anemia virus, feline immunodeficiency virus, and HTLV.

4. A nucleic acid construct as claimed in claim 1 wherein the first promoter sequence or enhancer sequence and the second promoter sequence or enhancer sequence are the same or different, but at least one is nonspecifically, cell-specifically, virus-specifically, metabolically, or cell-cycle-specifically activatable.

5. A nucleic acid construct as claimed in claim 1, wherein the chimeric promoter inhibits the expression of said transgene.

6. A nucleic acid construct as claimed in claim 1, wherein the nucleic acid is DNA.

7. A nucleic acid construct as claimed in claim 1, wherein the nucleic acid construct is a vector.

8. A nucleic acid construct as claimed in claim 1, wherein the transgene is a structural gene which encodes a therapeutically active compound selected from the group consisting of cytokines; growth factors; antibodies; antibody fragments; fusion proteins composed of a ligand and an enzyme; fusion proteins composed of a ligand and a cytokine; fusion proteins composed of a ligand and a growth factor; receptors for cytokines; receptors for growth factors; proteins having an antiproliferative effect; proteins having an apoptotic effect; proteins having a cytotoxic effect; angiogenesis inhibitors; thrombosis-inducing proteins; blood coagulation factor; coagulation inhibitors; fibrinolysis-inducing protein; complement-activating proteins; human C3b; modified C3b; bacterial proteins; virus coat proteins; parasitic antigens; peptides having an effect on the blood circulation; proteins having an effect on the blood circulation; and ribozymes.

9. A nucleic acid construct as claimed in claim 1 wherein the transgene is a structural gene which encodes a ribozyme which inactivates mRNA encoding a protein selected from the group consisting of cell-cycle control proteins, virus proteins, cytokines, growth factors, cytokine receptors and growth factor receptors.

10. A nucleic acid construct as claimed in claim 1 wherein the transgene is a structural gene which encodes an enzyme which cleaves a precursor of a drug, thereby forming the drug.

11. A nucleic acid construct as claimed in claim 1 wherein the transgene is a structural gene which encodes a ligand-enzyme fusion protein.

12. An isolated cell containing a nucleic acid construct as claimed in claim 1.

13. A cell transformed with a nucleic acid construct as claimed in claim 1.

14. A nucleic acid construct as claimed in claim 1, wherein the chimeric promoter is a promoter module selected from the group consisting of CDE-CHR and E2FBS-CHR.

15. A nucleic acid construct as claimed in claim 1, wherein the promoter sequence, enhancer sequence or activator sequence is selected from the group consisting of gene-regulatory nucleotide sequences which are activated in endothelial cells, smooth muscle cells, striated muscle cells, macrophages, lymphocytes, tumor cells, liver cells, leukemia cells and glia cells, or is selected from the group consisting of promoter sequences of HBV, HCV, HSV, HPV, EBV, HTLV, and HIV viruses.

16. A nucleic acid construct as claimed in claim 1, wherein the nuclear retention signal is an RRE sequence and the nuclear export factor is a rev protein.

17. A nucleic acid construct as claimed in claim 4 wherein said at least one promoter sequence or enhancer sequence is metabolically activatable by hypoxia.

18. A nucleic acid construct as claimed in claim 7, which is a plasmid vector.

19. A nucleic acid construct as claimed in claim 7, which is a viral vector.

20. A nucleic acid construct as claimed in claim 9, wherein the cell-cycle control protein is selected from the group consisting of cyclin A, cyclin B, cyclin D1, cyclin E, E2F1-5, cdc2, cdc25C, and DP1.

21. A nucleic acid construct as claimed in claim 11, wherein the ligand binds to proliferating endothelial cells and is selected from the group consisting of antibodies, antibody fragments, terminal mannose-containing proteins, cytokines, growth factors, and adhesion molecules.

22. A nucleic acid construct as claimed in claim 11, wherein the ligand binds to tumor cells.

23. A nucleic acid construct comprising:

(i) a nuclear retention signal selected from the group consisting of a rev-responsive element (RRE) of Human Immune Deficiency Virus-1 (HIV-1), an RRE of Human Immune Deficiency Virus-2 (HIV-2), an RRE-equivalent retention signal of a retrovirus and an RRE-equivalent retention signal of Hepatitis B virus (HBV), wherein said nuclear retention signal is operably linked to a transgene;

(ii) a first promoter sequence or enhancer sequence which activates basal transcription of the transgene;

(iii) a second promoter sequence or enhancer sequence which activates transcription of a nuclear export factor, wherein at least one of said first or second promoter sequences or enhancer sequences comprises an activator-responsive promoter unit having the following components:
a) at least a third promoter sequence or enhancer sequence which is non-specifically, virus-specifically, metabolically, cell-specifically and/or cell-cycle-specifically activatable,
b) at least one activator sequence which is located downstream of the third promoter sequence or enhancer sequence and is activated by the third promoter sequence or enhancer sequence, and
c) an activator-responsive promoter which is activated by the expression products of said at least one activator sequence; and
iv) a nucleic acid which encodes a nuclear export factor selected from the group consisting of a rev gene of HIV-1, a rev gene of HIV-2, a rev gene of maedi-visna virus, a rev gene of caprine arthritis encephalitis virus, a rev gene of equine infectious anemia virus, a rev gene of feline immunodeficiency virus, a rev gene of retroviruses and a rev gene of HTLV, wherein said nuclear export factor binds to a transcription product of the nuclear retention signal and thereby mediates transport of said transcription product of the transgene out of a cell's nucleus and into the cell's cytoplasm.

24. A nucleic acid construct as claimed in claim 23, wherein the first and/or second promoter sequence or enhancer sequence and/or the activator-responsive promoter is a chimeric promoter and said at least one activator sequence is a gene encoding at least one transcription factor which activates the chimeric promoter.

25. A nucleic acid construct as claimed in claim 23, wherein the activator-responsive promoter is a LexA operator in combination with a SV40 promoter, and said at least one activator sequence comprises a cDNA encoding LexA DNA-binding protein, whose 3' end is linked to a 5' end of a cDNA encoding Gal80 protein, said construct further comprising a second activator sequence comprising a cDNA encoding a Gal80-binding domain of Gal4 protein, whose 3' end is linked to a 5' end of a cDNA of SV40 large T antigen nuclear localization signal, whose 3' end is linked to a 5' end of a cDNA encoding a HSV-1 VP16 transactivating domain.

26. A nucleic acid construct as claimed in claim 23 wherein the activator-responsive promoter has one or more sequences for binding to a Gal4 protein in combination with at least one SV40 promoter and said at least one activator sequence has a cDNA encoding a DNA-binding domain of the Gal4 protein and a cDNA encoding Gal80, said construct further comprising a second activator sequence having a cDNA encoding a Gal80-binding domain of Gal4, a cDNA encoding SV40 nuclear localization signal and a cDNA encoding an HSV-1 VP16 acid transactivating domain.

27. A nucleic acid construct as claimed in claim 23 wherein said at least one activating sequence has a cDNA encoding SV40 nuclear localization signal; a cDNA encoding an HSV-1 VP16 acid transactivating domain; and a cDNA encoding a cytoplasmic moiety of a CD4 glycoprotein, said construct further comprising a second activating sequence having a cDNA encoding SV40 nuclear localization signal, a cDNA encoding a DNA-binding domain of a Gal4 protein and a cDNA encoding a CD4-binding sequence of p56 lck protein.

28. A nucleic acid construct as claimed in claim 23 wherein the promoter sequence, enhancer sequence or activator sequence is selected from the group consisting of gene-regulatory nucleotide sequences which are activated in endothelial cells, smooth muscle cells, striated muscle cells, macrophages, lymphocytes, tumor cells, liver cells, leukemia cells and glia cells, or is selected from the group consisting of promoter sequences of HBV, HCV (Hepatitis C virus), HSV (Herpes simplex virus), HPV (Human papilloma virus), EBV (Epstein-Barr virus), HTLV or HIV viruses.

29. A nucleic acid construct as claimed in claim 23, wherein a 5' end of the nuclear retention signal is linked directly or indirectly to a 3' end of the transgene.

30. A nucleic acid construct as claimed in claim 23, wherein a transcription product of the nuclear retention signal possesses a structure for binding to a nuclear factor selected from the group consisting of a rev-gene of the viruses HIV-1, HIV-2, maedi-visna virus, caprine arthritis encephalitis virus, equine infectious anemia virus, feline immunodeficiency virus, and HTLV.

31. A nucleic acid construct as claimed in claim 23, wherein the first promoter sequence or enhancer sequence and the second promoter sequence or enhancer sequence are the same or different, but at least one is nonspecifically, cell-specifically, virus-specifically, metabolically, or cell-cycle-specifically activatable.

32. A nucleic acid construct as claimed in claim 23, wherein at least one of said first or second promoter sequences or enhancer sequences is a chimeric promoter which interacts with an adjacent, upstream, cell-specifically, virus-specifically or metabolically activatable activator sequence which influences the expression of said transgene.

33. A nucleic acid construct as claimed in claim 23, wherein the nucleic acid is DNA.

34. A nucleic acid construct as claimed in claim 23, wherein the nucleic acid construct is a vector.

35. A nucleic acid construct as claimed in claim 23, wherein the transgene is a structural gene which encodes a therapeutically active compound selected from the group consisting of cytokines; growth factors; antibodies, antibody fragments; fusion proteins composed of a ligand and an enzyme; fusion proteins composed of a ligand and a cytokine; fusion proteins composed of a ligand and a growth factor; receptors for cytokines; receptors for growth factors; proteins having an antiproliferative effect; proteins having an apoptotic effect; proteins having a cytotoxic effect; angiogenesis inhibitors; thrombosis-inducing proteins; blood coagulation factor; coagulation inhibitors; fibrinolysis-inducing protein; complement-activating proteins; human C3b; modified C3b; bacterial proteins; virus coat proteins; parasitic antigens; peptides having an effect on the blood circulation; proteins having an effect on the blood circulation; and ribozymes.

36. A nucleic acid construct as claimed in claim 23, wherein the transgene is a structural gene which encodes a ribozyme which inactivates mRNA encoding a protein selected from the group consisting of cell-cycle control proteins, virus proteins, cytokines, growth factors, cytokine receptors and growth factor receptors.

37. A nucleic acid construct as claimed in claim 23, wherein the transgene is a structural gene which encodes an enzyme which cleaves a precursor of a drug, thereby forming the drug.

38. A nucleic acid construct as claimed in claim 23, wherein the transgene is a structural gene which encodes a ligand-enzyme fusion protein.

39. An isolated cell containing a nucleic acid construct as claimed in claim 23.

40. A cell transformed with a nucleic acid construct as claimed in claim 23.

41. A nucleic acid construct as claimed in claim 23, wherein the nuclear retention signal is an RRE sequence and the nuclear export factor is a rev protein.

42. A nucleic acid construct as claimed in claim 31, wherein said at least one promoter sequence or enhancer sequence is metabolically activatable by hypoxia.

43. A nucleic acid construct as claimed in claim 32, wherein the chimeric promoter inhibits the expression of said transgene.

44. A nucleic acid construct as claimed in claim 32, wherein the chimeric promoter is a promoter module selected from the group consisting of CDE-CHR and E2FBS-CHR.

45. A nucleic acid construct as claimed in claim 34, which is a plasmid vector.

46. A nucleic acid construct as claimed in claim 34, which is a viral vector.

47. A nucleic acid construct as claimed in claim 36, wherein the cell-cycle control protein is selected from the group consisting of cyclin A, cyclin B, cyclin D1, cyclin E, E2F1-5, cdc2, cdc25C, and DP1.

48. A nucleic acid construct as claimed in claim 38, wherein the ligand binds to proliferating endothelial cells and is selected from the group consisting of antibodies, antibody fragments, terminal mannose-containing proteins, cytokines, growth factors, and adhesion molecules.

49. A nucleic acid construct as claimed in claim 38, wherein the ligand binds to tumor cells.

* * * * *